(12) United States Patent
Lakowicz et al.

(10) Patent No.: US 6,395,556 B1
(45) Date of Patent: May 28, 2002

(54) POLARIZATION BASED SENSING

(76) Inventors: Joseph R. Lakowicz, 10037 Fox Den Rd., Ellicott City, MD (US) 20142; Ignacy Gryczynski, 14 Minte Dr., Baltimore, MD (US) 21236; Zygmunt Gryczynski, 4713 Roundhill Rd., Ellicott City, MD (US) 21043

( * ) Notice: Subject to any disclaimer, the term of this patent is extended or adjusted under 35 U.S.C. 154(b) by 0 days.

(21) Appl. No.: 09/831,625

(22) PCT Filed: Nov. 10, 1999

(86) PCT No.: PCT/US99/26463

§ 371 (c)(1),
(2), (4) Date: Aug. 7, 2001

(87) PCT Pub. No.: WO00/28307

PCT Pub. Date: May 18, 2000

Related U.S. Application Data

(60) Provisional application No. 60/107,997, filed on Nov. 11, 1998.

(51) Int. Cl.$^7$ .............................................. G01N 21/64
(52) U.S. Cl. ..................... 436/68; 436/95; 436/138; 436/172; 422/82.07; 422/82.08; 422/91
(58) Field of Search ................... 356/366, 367, 356/368, 370; 250/458.1, 459.1; 422/82.06, 82.07, 82.08, 91; 436/68, 95, 138, 172

(56) References Cited

U.S. PATENT DOCUMENTS

| | | | |
|---|---|---|---|
| 4,516,856 A | | 5/1985 | Popelka |
| 5,660,991 A | * | 8/1997 | Lakowicz et al. ............ 435/7.1 |
| 5,756,292 A | * | 5/1998 | Royer ......................... 250/372 |
| 5,876,672 A | * | 3/1999 | Dandliker et al. ........ 250/458.1 |
| 6,025,917 A | * | 2/2000 | Toyonaga et al. ............ 250/225 |
| 6,284,544 B1 | * | 9/2001 | Thompson et al. ......... 436/166 |

* cited by examiner

Primary Examiner—Jeffrey Snay
(74) Attorney, Agent, or Firm—Rothwell, Figg, Ernst & Manbeck

(57) ABSTRACT

The present invention relates to the determination of the presence or concentration of an analyte in a sample by visual or electronic element, using polarization based sensing techniques (14) employing fluorescent sensing (11) and reference molecules (10).

22 Claims, 22 Drawing Sheets

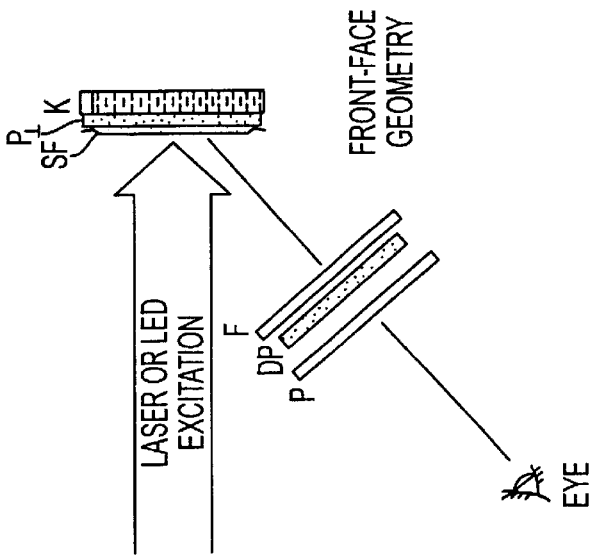

- K - CUVETTE
- SF - STRETCHED PVA FILM DOPED WITH HIGHLY ORIENTED DYE; PROVIDES CONSTANT VERTICALLY POLARIZED FLUORESCENCE BACKGROUND.
- $P_\perp$ - THIN FILM POLARIZER ORIENTED ORTOGONALLY TO SF; TRANSMITS HORIZONTAL COMPONENT OF INVESTIGATED FLUORESCENCE
- F - FILTER; TRANSMITS FLUORESCENCE, ELIMINATES SCATTERED EXCITATION
- DP - DUAL POLARIZER; PLATE COMBINED WITH TWO "HALF MOON" POLARIZERS
- P - POLARIZER MOUNTED IN ROTARY STAGE

FIG. 13B

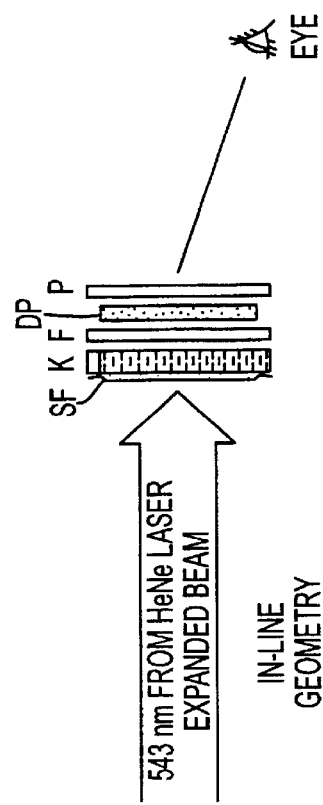

- K - CUVETTE
- SF - STRETCHED PVA FILM DOPED WITH HIGHLY ORIENTED DYE; PROVIDES CONSTANT VERTICALLY POLARIZED FLUORESCENCE BACKGROUND.
- $P_\perp$ - THIN FILM POLARIZER ORIENTED ORTOGONALLY TO SF; TRANSMITS HORIZONTAL COMPONENT OF INVESTIGATED FLUORESCENCE
- F - FILTER; TRANSMITS FLUORESCENCE, ELIMINATES SCATTERED EXCITATION
- DP - DUAL POLARIZER; PLATE COMBINED WITH TWO "HALF MOON" POLARIZERS
- P - POLARIZER MOUNTED IN ROTARY STAGE

FIG. 13A

POLARIZATION BASED SENSING

CROSS-REFERENCES TO RELATED APPLICATIONS

This application claims the benefit of application Ser. No. 60/107,997 filed Nov. 11, 1998.

STATEMENT REGARDING FEDERALLY SPONSORED RESEARCH OR DEVELOPMENT

The work described herein was supported by a grant from the National Institutes of Health National Center for Research Resources RR-08119.

BACKGROUND OF THE INVENTION

1. Field of the Invention

The present invention relates to the determination of the presence or concentration of an analyte in a sample by visual or electronic means, using polarization based sensing techniques employing fluorescent sensing and reference molecules.

2. Description of the Related Art

A bibliography follows at the end of the Detailed Description of the Invention. The listed references are all incorporated herein by reference.

During the past ten years there have been remarkable advances in the technology for fluorescence sensing [1–7]. There has been extensive development of new fluorescent probes [8–10], and the introduction of time-resolved fluorescence to chemical sensing, which is referred to as lifetime-based sensing [11–13]. Additionally, the timescale of fluorescence has been extended from the nanosecond range to the microsecond range by the use of long-lifetime metal-ligand complexes [14–15].

New approaches to fluorescence sensing continue to appear. Recently a new approach to sensing has been developed which uses reference fluorophores in addition to the sensing fluorophores. The concept is to mix a sensing fluorophore which is sensitive to an analyte with a second fluorophore which is not sensitive to the analyte. One then measures the combined emission of the sensor and reference fluorophores, which can be used to determine the analyte concentration. This approach has been used with the long lifetime metal-ligand complexes (MLC) as the reference fluorophore, and a pH sensitive probe, to determine pH or $pCO_2$ from the phase angle of the emission [16–17]. The present inventors have also used such mixtures to determine pH, calcium, and glucose concentrations. In our studies we used the low frequency modulation of the emission, rather than the phase angle, to determine the analyte concentration [18–21]. We showed that the low frequency modulation can be used to determine the fractional intensity of the nanosecond fluorophore, relative to that of the metal-ligand complex with its microsecond decay time.

In a recently published paper [22], the present inventors extended the idea of using a reference fluorophore to sensing based on anisotropy measurements. The concept is based on the additivity of anisotropy [23–25]. This rule states that the anisotropy for a mixture of fluorophores is the weighted average of the value for each fluorophore and their fractional contributions to the total intensity. Thus, an intensity change of the sensing fluorophore is transformed into a change in anisotropy or polarization by appropriate placement of polarizers. We developed sensing methods in which the reference was a fluorophore in a stretch-oriented film of polyvinyl alcohol. We used anisotropy-based sensing to measure pH using 6-carboxy fluorescein or the concentration of labeled protein in the sample.

However, there remains a need in the art for improved methods for determining the presence or concentration of an analyte using fluorescent reference and sensing molecules.

BRIEF SUMMARY OF THE INVENTION

In one aspect, the present invention relates to a method for determining the presence or concentration of an analyte, comprising the steps of:

a) providing a fluorescent reference molecule and a fluorescent sensing molecule;

b) exposing said sensing molecule to an analyte to form a mixture, wherein said analyte is capable of changing the intensity of the fluorescence emitted by the sensing molecule in a concentration-dependent manner;

c) exposing said reference molecule and said mixture to a radiation source which causes said reference and sensing molecules to emit fluorescence;

d) polarizing said emitted fluorescence through two different polarization axes which are substantially perpendicular to each other;

e) attenuating the emission from one of the polarization axes, if necessary, such that the intensities of the emissions through both axes are substantially equal; and f) correlating the degree of attenuation with the presence or concentration of said analyte in said sample.

In another aspect, the present invention relates to a sensor for determining the presence or concentration of an analyte in a sample, which comprises:

a) a fluorescent reference molecule;

b) a fluorescent sensing molecule, wherein said analyte is capable of changing the intensity of the fluorescence emitted by the sensing molecule in a concentration-dependent manner;

c) optionally a radiation source which is capable of causing said reference and sensing molecules to emit fluorescence;

d) means for isolating said emitted fluorescence along two different polarization axes which are substantially perpendicular to each other; and e) means for attenuating the emission from one of the polarization axes, such that the intensities of the emissions through both axes are substantially equal.

BRIEF DESCRIPTION OF THE DRAWINGS

FIG. 13 depicts two optical systems for anisotropy-based sensing with visual detection. FIG. 13A depicts an in-line geometry with a stretched film. FIG. 13B depicts a front-face geometry. In the front-face geometry with the stretched film it is possible to use an additional polarizer $P_\perp$, which allows selective detection of horizontal component of the fluorescence from the sample cuvette K. Such a configuration extends the range of angles (angles needed to equalize the transmittance of both polarizers in DP) to 90°. Front-face anisotropy sensing can be performed without the additional polarizer, resulting in the 45° range of angles.

FIG. 14 depicts polarizer angles for in-line anisotropy sensing.

FIG. 19A shows the emission spectra of the vertical component and of the horizontal component. The calcium concentration is constant at 1.35 micro molar in the left side of the sensor. The calcium concentration is variable in the right side of the sensor.

DETAILED DESCRIPTION OF THE INVENTION

The present invention provides a new approach to fluorescence sensing which optionally relies on visual determination of the polarization and fluorescent reference and sensing molecules.

The present invention may be used to detect any analyte for which a suitable fluorescent sensing probe is available, i.e., a sensing molecule whose fluorescent emission changes upon exposure to the analyte in a concentration-dependent manner. Many such molecules are well-known, and may be used to measure pH, glucose, oxygen, blood gases, various ions, proteins, etc.

The fluorescent reference molecule is chosen to provide a constant reference or background. There are a wide range of commercially available suitable reference molecules, for example those sold by Molecular Probes, Inc., Eugene, Oreg. and other companies. The reference molecule may be a distinct entity but having the same structure as the sensing molecule, provided that the reference molecule is not exposed to the analyte, e.g., is isolated in a separate compartment or the like. In a preferred embodiment, the reference molecule is embedded in an oriented film which is not effected by the analyte.

In practice, the sensing molecule is exposed to a sample containing an analyte of interest. The reference and sensing molecules are then exposed to a radiation source which causes the molecules to emit fluorescence. The choice of the radiation source will depend on a number of factors, such as the fluorescent characteristics of the reference and sensing molecules, the specific application, etc. Preferred sources include HeNe lasers, blue LEDs, sunlight and room light.

The fluorescent emission from the reference and sensing molecules is then polarized along two substantially perpendicular polarization axes. That is preferably accomplished by allowing the emission from each molecule to pass through a dual polarizer, with adjacent sections oriented substantially orthogonally to each other. Optionally, before passing through the dual polarizer, the emitted fluorescence is allowed to pass through a filter which substantially eliminates scattered excitation.

Figure 21:
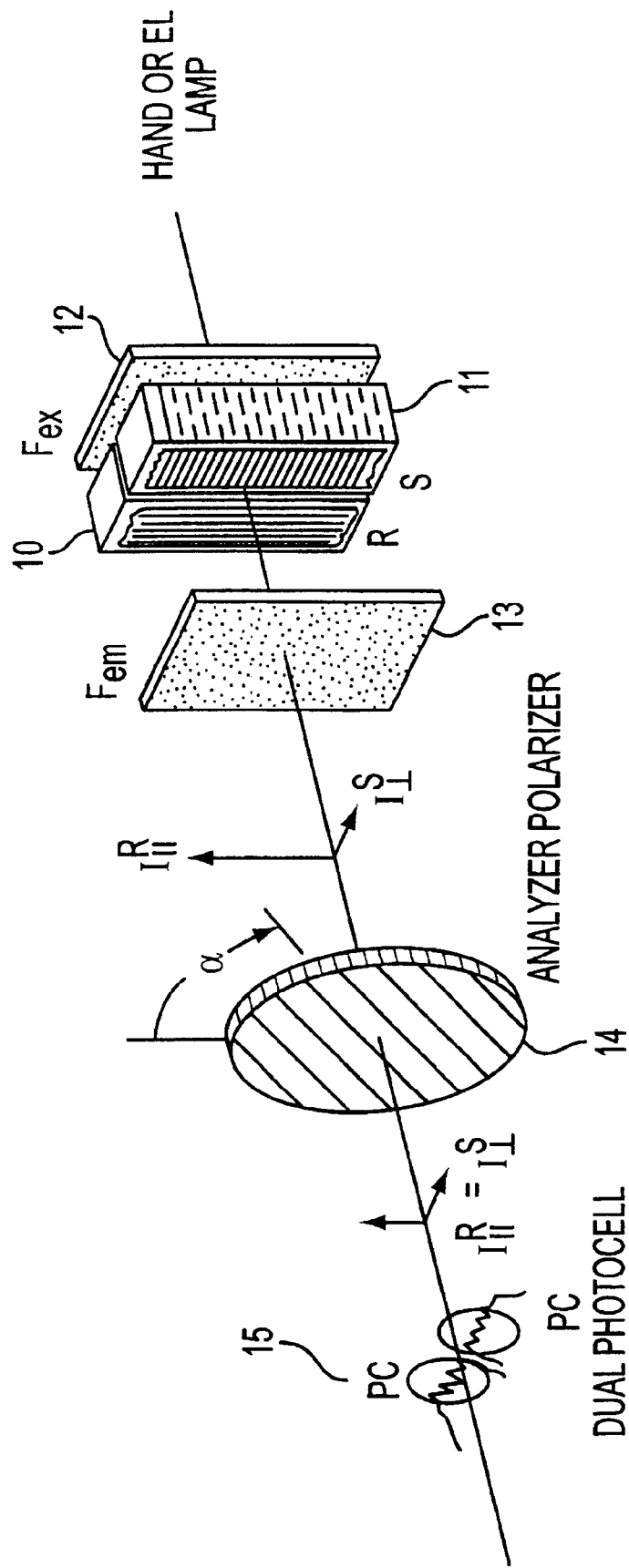
FIG. 21 schematically depicts an apparatus for polarization sensing with photocell detection according to present invention. The value of a is 0° with the analyzer polarizer is oriented vertically.
Figure 22:
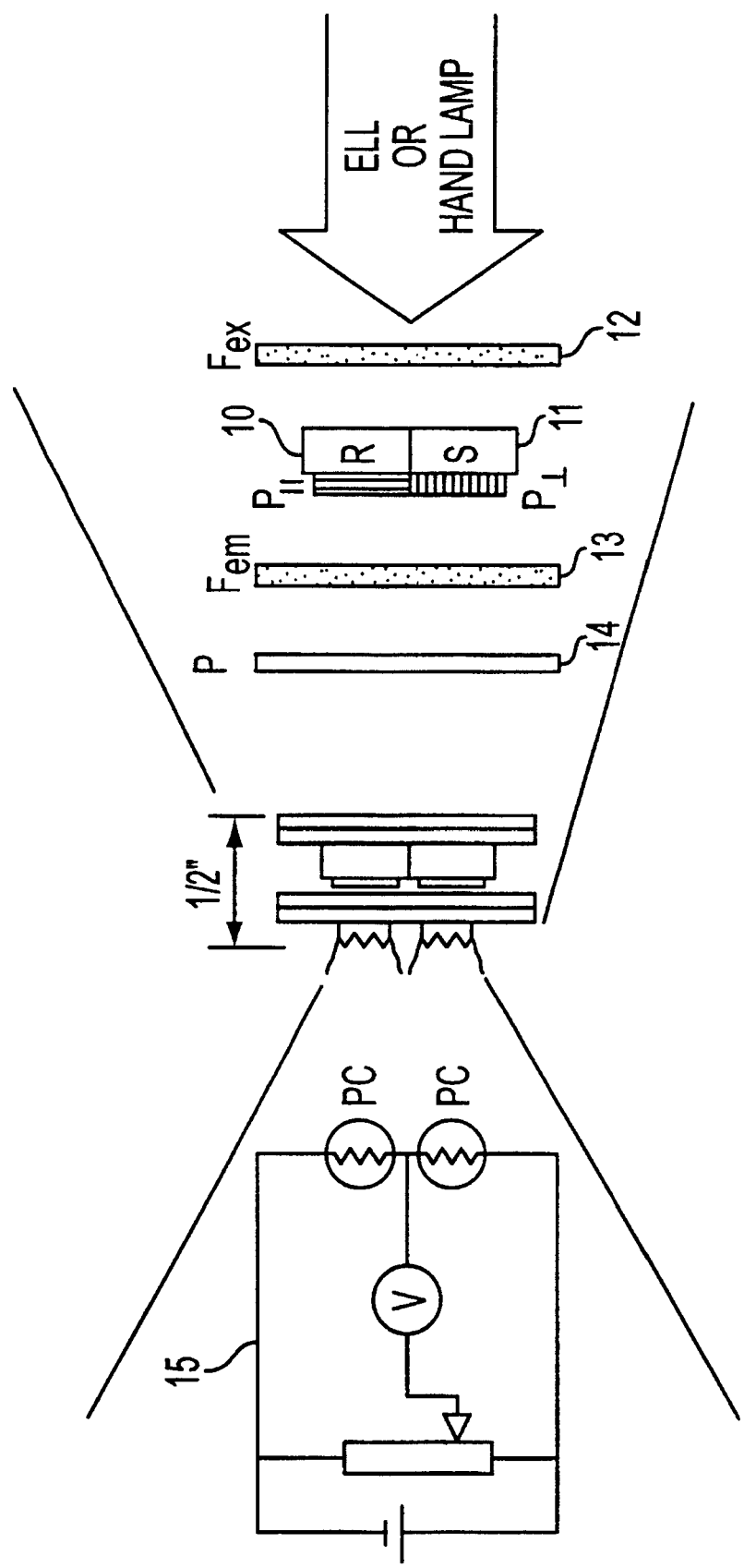
FIG. 22 schematically depicts an apparatus for polarization sensing with photocell detection according to the present invention. The expanded view on the right side of the figure shows optical components. The expanded view on the left side of the figure shows the detector with bridged photocells. The polarizer P is rotated until the signal on the volt meter is null.

After the emission is isolated along the two polarization axes, it will generally be the case that the two emissions will have different intensities. In the next step, the intensities are substantially equalized. That may be accomplished by, e.g., allowing the output from the dual polarizer to pass through an analyzer polarizer, which may be rotated until both intensities are substantially equal. The determination of when the intensities are substantially equal in the simplest case may be made visually, or it may be made electronically by means which would be readily apparent to those skilled in the art. For example, the intensities may be measured in independent detectors, and the analyzer polarizer may be adjusted until the signals are equal. Alternatively, one could use the ratio of two signals and adjust the ratio to unity. In still another embodiment, the output from the two detectors could be used in a balanced circuit, such as a Wheatstone bridge. The degree of rotation needed, relative to an initial reference position (for the emission from the reference molecule in the absence of the sensing molecule) is then correlated with the presence or concentration of the analyte. One suitable electronic detector is depicted in FIGS. 21 and 22, in which the apparatus comprises filter 12, containers 10 and 11 which house the reference and sensing molecules, filter 13, analyzer polarizer 14, and dual photocell 15. In FIGS. 21 and 22, container 10 has on its surface a polarizing film oriented vertically, and container 11 has on its surface a polarizing film oriented horizontally.

The foregoing approach has used to measure the concentration of RhB in intralipid, and to measure pH using 6-carboxy-fluorescein. The analyzer angle is typically accurate to one degree, providing pH values accurate to ±0.1 pH unit at the mid-point of the titration curve.

The present invention further relates to a method of visual polarization sensing which does not require an oriented film, and which can use the same fluorophore for the sample and reference. These approaches to visual sensing are generic and can be applied to a wide variety of analytes for which fluorescent probes are available. Importantly, the devices are simple, with the only electronic component being the light source.

Theory—In-Line Geometry

In the biophysical use of fluorescence it is common to use the anisotropy of the emission. However, in connection with the present invention it is possible to visually observe the emission from the front surface (front-face geometry) or directly through (in-line) the sample (in-line geometry). For these geometric conditions it is easier to describe the results in terms of the polarization of the emission, $$P = \frac{I^{\parallel} - I^{\perp}}{I^{\parallel} + I^{\perp}} \quad (2)$$

where $I^{\parallel}$ and $I^{\perp}$ mare the intensities seen parallel ($\parallel$) or perpendicular ($\perp$) to the orientation of the reference film.

Figure 14A:
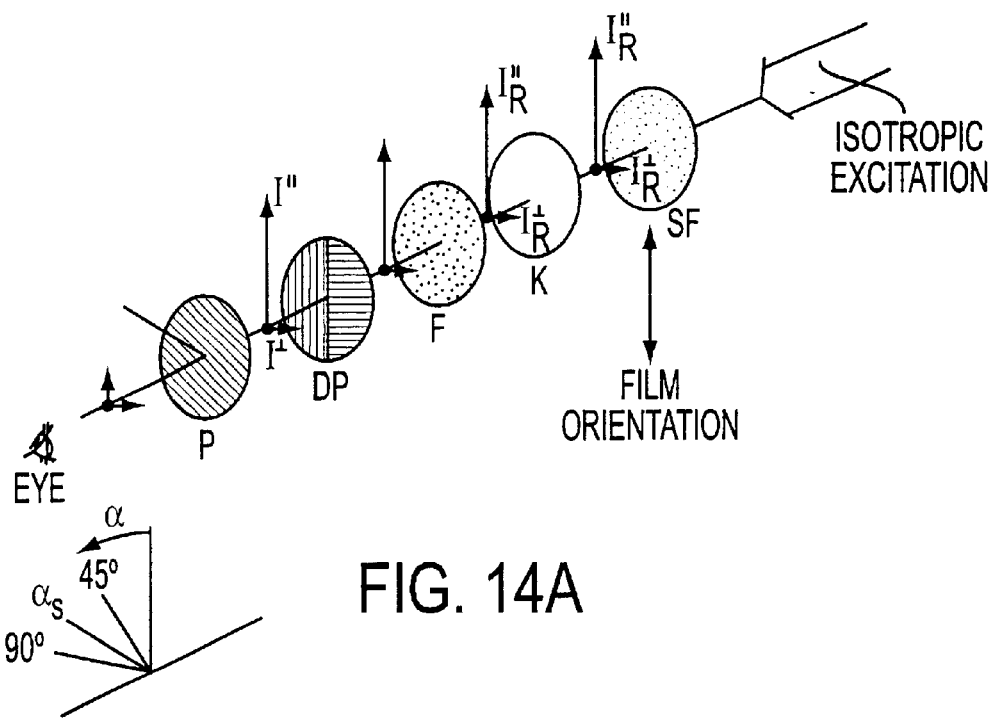
In FIG. 14A there is no emission from the sample. For a strongly oriented reference the initial polarizer angle is near 90° from the vertical.
Figure 14B:
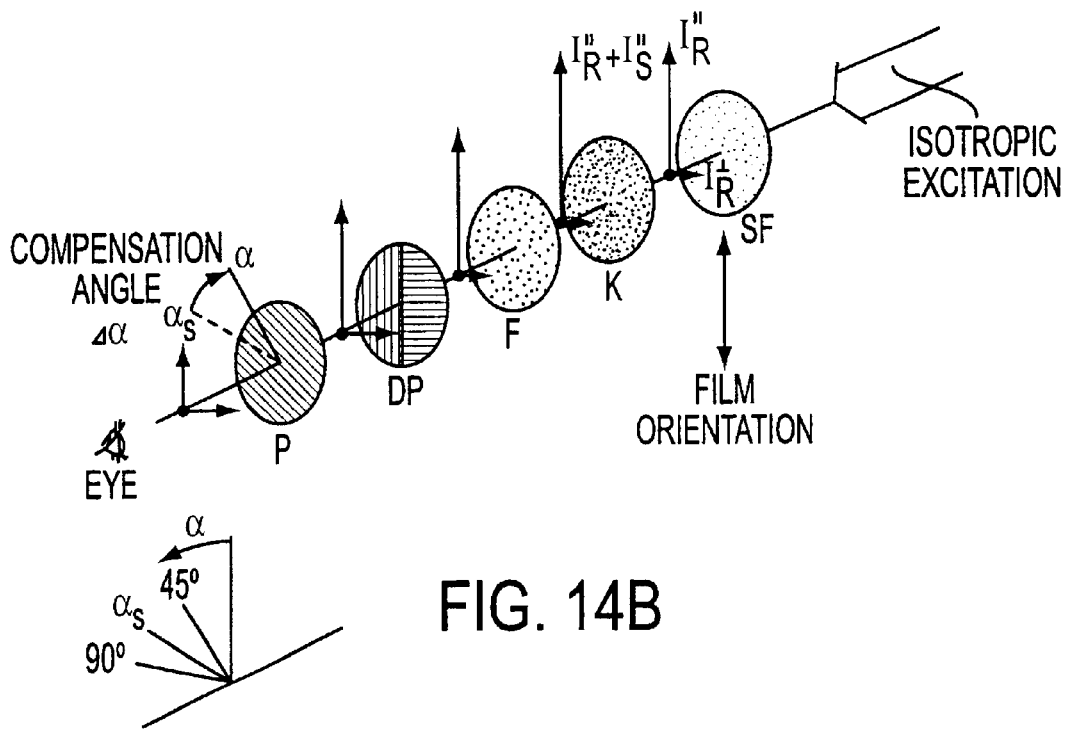
In FIG. 14B the sample emission is dominant, and the angle is near 45° from the vertical.

The theory for visual detection of the polarization can be developed using FIG. 14. This scheme shows the various polarized intensities from the sample (S) and reference (R) which are present along the optical path. Suppose the sample is illuminated with unpolarized light. The emission from the stretched film is polarized along its stretch axis ($I_R^{\parallel}$). Since the alignment is never perfect, there is also a smaller component perpendicular to the stretch axis ($I_R^{\parallel}$). The starting angle of the polarizer measured from the vertical axis ($\alpha_0$) will be near 90°. The angle will be near 90° because the film emission is highly polarized, and the vertical component ($I_R^{\perp}$) must be significantly attenuated to yield equal intensities in each half of the dual polarizer.

Suppose now there is significant emission from the sample (FIG. 14, lower panel). Since the excitation is not polarized, and the sample is not oriented, the sample adds components of equal intensity in both directions ($I_S^{\parallel}=I_S^{\perp}$) We have assumed that the stretched film is optically thin, so that it does not act like a polarizer. The emission transmitted through each side of the dual polarizer is the sum of the two polarized components $$I^{\parallel}=I_R^{\parallel}+I_S^{\parallel} \quad (3)$$

$$I^{\perp}=I_R^{\perp}+I_S^{\perp}. \quad (4)$$

Assume now that these two components are observed through the analyzer polarizer. The intensities observed through the vertical (V) and horizontal (H) regions of the dual polarizer (DP) are given by $$I^V=(I_R^{\parallel}+I_S^{\parallel})\cos^2 \alpha \quad (5)$$

$$I^H=(I_{R\perp}+I_S^{\perp})\sin^2 \alpha \quad (6)$$

where $\alpha$ is the analyzer polarizer angle from the vertical position.

For visual measurement the analyzer is rotated until the intensity is equal for both sides of the dual polarizer. For this condition one has $$(I_R^{\parallel}+I_S^{\parallel})\cos^2 \alpha (I_R^{\perp}+I_S^{\perp})\sin^2 \alpha \quad (7)$$

and $$\tan^2 \alpha = \frac{I_R^{\parallel} + I_S^{\parallel}}{I_R^{\perp} + I_S^{\perp}}. \quad (8)$$

The stretched film displays a constant polarization value, which can be defined in terms of the ratio of the polarized intensities, $$k=I_R^{\parallel}/I_R^{\perp} \quad (9)$$

For an isotropic film there is no polarization and k=1. Hence the initial angle for the analyzer polarizer is given by $\tan^2 \alpha_0=1.0$ or $\alpha_0=45°$. For a perfectly oriented film k=infinity, $\tan^2 \alpha_0$ is very large so that $\alpha_0$ is near 90°. In practice one obtains highly but imperfectly oriented samples with values of k ranging from 10 to 12 in the case of isotropic excitation.

It is instructive to examine how the polarizer angle depends on the relative fluorescence intensity from the sample and the reference. Let the total intensity from the reference be defined as $$I_R^T=I_R^{\parallel}+I_R^{\perp}. \quad (10)$$

Dividing the numerator and denominator in eq. 8 by $I_R^T$ yields $$\tan^2\alpha = \frac{\frac{k}{k+1} + \frac{I_S^{\|}}{I_R^T}}{\frac{1}{k+1} + \frac{I_S^{\perp}}{I_R^T}}. \quad (11)$$

For many situations the emission from the sample will be unpolarized, $I_S^{\|}=I_S^{\perp}$. For this condition one can define the ratio n, which is the ratio of the total emission from the sample to that of the reference, $$n = \frac{I_S^T}{I_R^T} = \frac{I_S^{\|} + I_S^{\perp}}{I_R^T}. \quad (12)$$

Introduction of this ratio into eq. 11 yields $$\tan^2\alpha = \frac{\frac{k}{k+1} + \frac{n}{2}}{\frac{1}{k+1} + \frac{n}{2}}. \quad (13)$$

This expression (eq. 13) describes the angle of the polarizer needed to equalize the intensities in terms of the polarization ratio of the reference (k) and the relative intensity of the sample to that of the reference (n).

It is informative to examine the range of polarizer angles which can occur as the intensity of the sample increases. The initial condition ($\alpha_0$) is found when there is no emission from the sample, so that all the signal originates with the reference film. If the emission from the film were completely polarized (k=∞) then the analyzer would need to be oriented at 90° to equalize the intensities to zero. Basically, one would have to nearly extinguish the signal $I_R^{\|}$ by orienting the analyzer nearly perpendicular to the film axis.

In practice, the emission from the film is not completely polarized, but is defined by a finite value of the k value. For a typical value of k=12 the initial angle $\alpha_0$ with no fluorescence from the sample is about 74°, which can be found using eq. 13 with n=0. Alternatively, one can calculate $\alpha_0$ using $$\tan \alpha_0 = \sqrt{k}. \quad (14)$$

Now consider the condition when the emission from the sample is the dominant emission. We also assume that the sample emission is not polarized. Under these conditions the intensities $I^V$ and $I^H$ will be equal yielding $\tan^2\alpha=1.0$. The intensities seen through the analyzer will be equal when the analyzer is rotated 45° from the vertical. This value can be found by noting that as n becomes much larger than k, tan a approaches unity (eq. 13) so a approaches 45°.

It is convenient to examine the changes in polarizer angle ($\Delta\alpha$) in the absence and presence of sample. We call this value the "compensation angle." This change in angle is given by $$\Delta\alpha = \alpha_0 - \alpha = \arctan\sqrt{k} - \arctan\sqrt{\frac{\frac{k}{k+1} + \frac{n}{2}}{\frac{1}{k+1} + \frac{n}{2}}}. \quad (15)$$

Figure 1A:
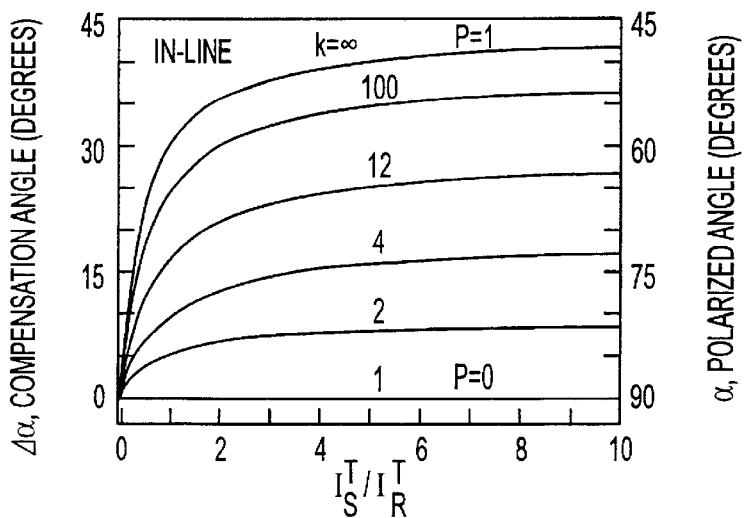
FIG. 1 shows the calculated compensation angles for in-line anisotropy sensing (FIG. 1A) and front-face anisotropy sensing (FIGS. 1B and 1C). The lower two panels are similar, except for the scale of the x-axis.

Simulated values of $\Delta\Delta$ are shown in FIG. 1A. These values were calculated for various values of k, and for a 10-fold range of relative intensities $n=I_S^T/I_R^T$. In the absence of fluorescence from the sample the polarizer remains at the initial value near 90° with $\Delta\alpha=0$. As the sample intensity increases the polarizer must be rotated towards 45° to equalize the intensities. For experimentally accessible values of k near 12, the range of $\Delta\alpha$ values is about 30 degrees. When using the in-line geometry without the additional polarizer ($P_\perp$ in FIG. 13) the range of angles depends on the orientation (k) of the film. The film must be oriented to some extent (k>1) otherwise there is no change in the compensation angle. More highly oriented films, or larger values of k, yield larger changes in $\alpha$.

Theory-Front Face Geometry

The operational principles of the front face polarization sensor (FIG. 13, lower panel) can be understood by similar reasoning. The front face sensor can be used without the extra polarizer $P_\perp$, in which case the range of angles is the same described above for the in-line geometry. An alternative approach is to use a polarizer $P_\perp$ in front of the sample. This polarizer selects for the perpendicular component of the sample emission. Under this condition, $I_S^{\|}$ is zero. Assuming the sample emission is unpolarized, the total emission from the sample is $I_S^T=I_S^{\perp}$, and eq. 11 becomes $$\tan^2\alpha = \frac{\frac{k}{k+1}}{\frac{1}{k+1} + n}. \quad (16)$$

Figure 15A:
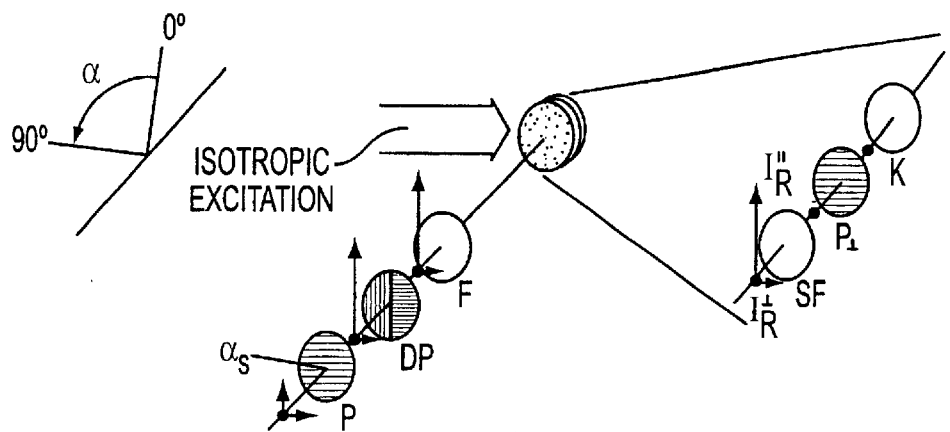
In FIG. 15A there is no emission from the sample. For a strongly oriented reference film the initial polarizer angle is near 90° from the vertical.
Figure 15B:
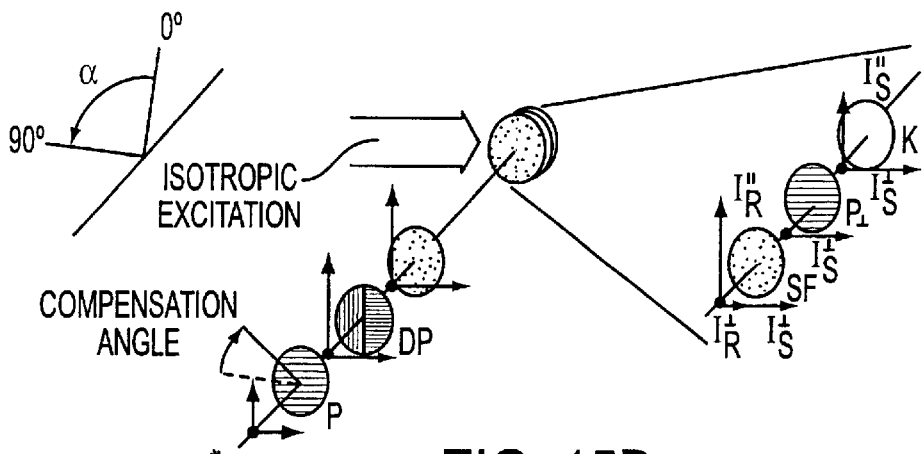
FIG. 15 depicts various polarizer angles for front-face anisotropy sensing.
In FIG. 15C the sample emission is dominant, and the angle approaches 0° from the vertical.
Figure 15C:
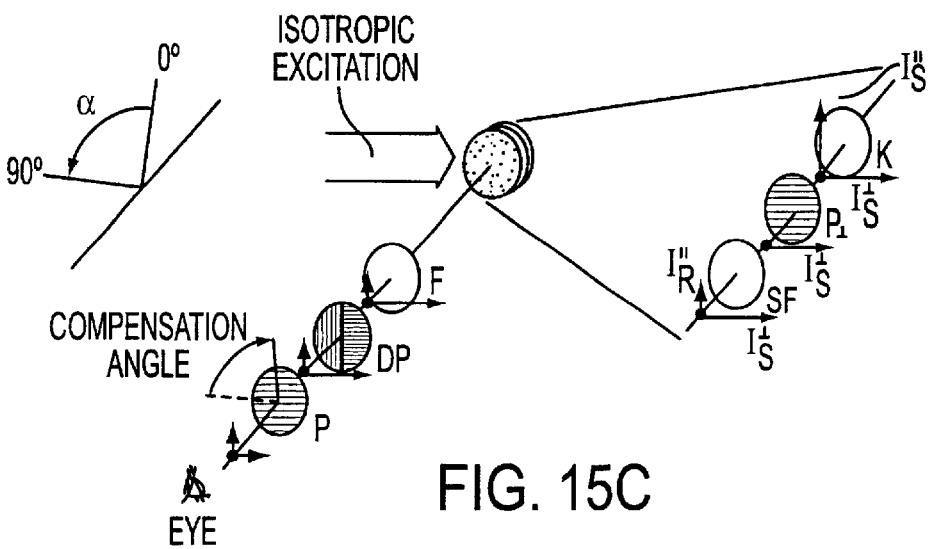

The limiting conditions for the front face sensor can be understood from FIG. 15. In the absence of emission from the sample the polarizer angle $\alpha_0$ is defined by the value of k. For a perfectly aligned reference film (k=∞) the analyzer polarizer must be oriented near 90° to equalize the intensities (top). At intermediate sample intensities (middle panel) the value of a to equalize the intensities will be between 0 and 90°. If emission from the sample is the dominant emission, then most of the emitted light is horizontally polarized, and the polarization angle must be near zero to equalize the signals (lower panel). This can be seen from eq. 16. As n becomes large, tan a approaches zero, so a approaches zero. This result illustrates an important effect of using the additional polarizer $P_\perp$. The range of polarization angles doubles to 90° as compared to the in-line geometry without the polarizer $P_\perp$.

For the front-face sensor the compensation angles $\Delta\alpha$ are given by $$\Delta\alpha = \alpha_0 - \alpha = \arctan\sqrt{k} - \arctan\sqrt{\frac{\frac{k}{k+1}}{\frac{1}{k+1} + n}}. \quad (17)$$

Figure 1B:
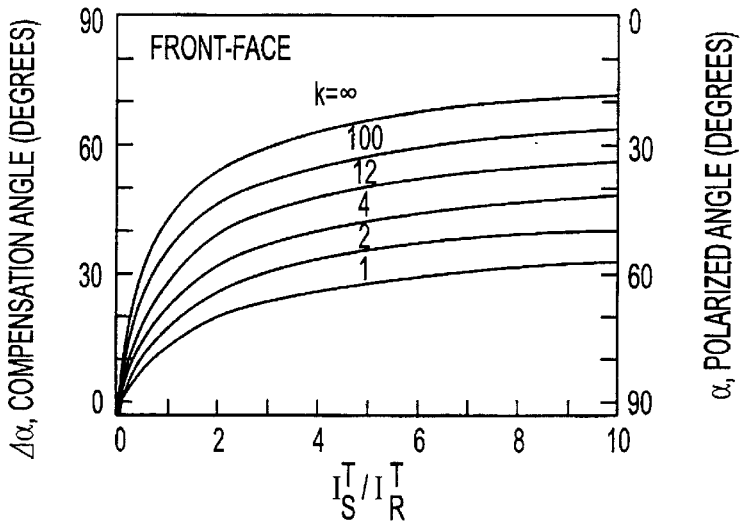
Figure 1C:
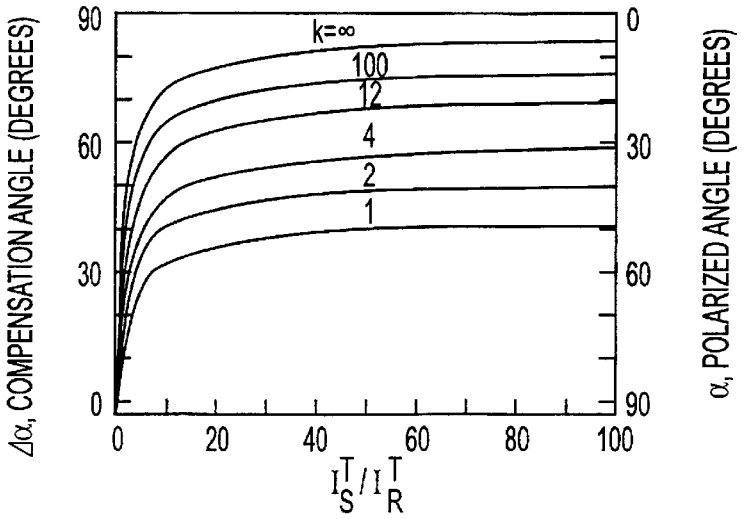

Simulated values of $\Delta\alpha$ are shown in FIG. 1, middle and lower panels. As the sample intensity increases the value of $\Delta\alpha$ approaches 90°. For available values of k near 12, $\Delta\alpha$ can be as large as 60°. Compared to the in-line geometry it seems that a greater range of sample intensities can be measured using the front-face geometry than using the in-line geometry (lower panel).

The simulated values of $\Delta\alpha$ for the front-face geometry reveal another possibility, which is to perform anisotropy sensing without an oriented sample. This can be seen in FIG. 1 (middle and lower panels) for k=1, which is an unpolarized reference. A range of 45° is available using even an unpolarized reference. This possibility results from the additional polarizer $P_\perp$ which transmits only one polarized component from the sample. Since the reference can be unpolarized, the reference can consist of the sensing fluorophore itself, rather than a different fluorophore in an oriented film.

Precision of Polarization Sensing with Visual Detection

The principle of polarization sensing with visual detection is to equalize the light intensities transmitted through both sides of the dual polarizer. In our initial experiments we were surprised to find that the polarizer angle could be determined to within 1°. The relative intensities change slowly for values of $\alpha$ near 45°, so that the precision we observed seemed to be unexpectedly high. For this reason we performed analyses to determine the expected precision of the $\alpha$ values.

The error in determining a should depend on the initial value of $\alpha(\alpha_0)$, the accuracy of the rotary stage, and the sensitivity of our eyes to detect the intensity differences. Our rotary stage was accurate to 1°, and more accurate stages are readily available. Hence we considered the effects of various values of $\alpha_0$ and the eye sensitivity. From eq. 5 one can show that the relative intensity through each side of the dual polarizer is given by $$I^H/I_V = \tan^2 \alpha. \quad (18)$$

Figure 2:
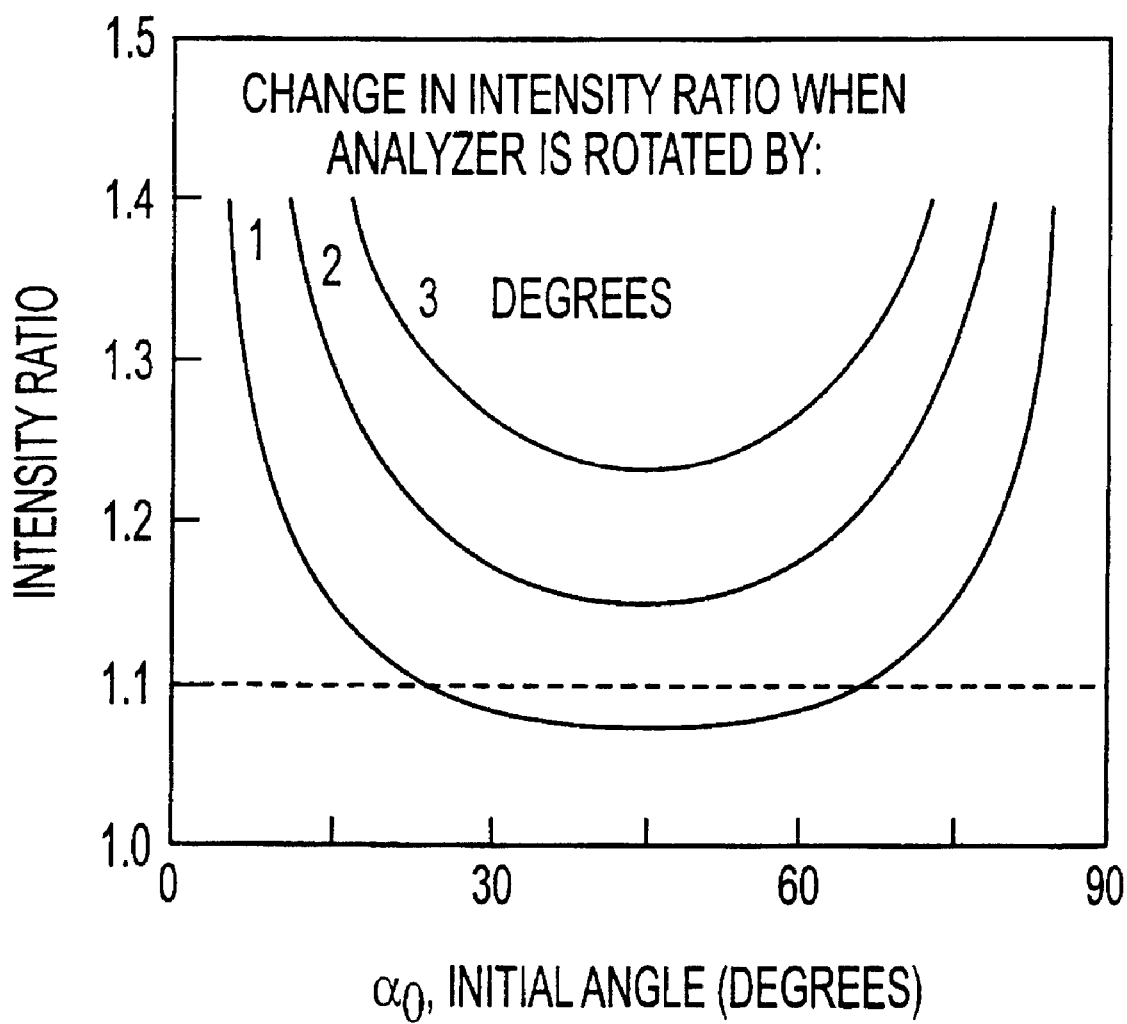
FIG. 2 shows the dependence of the intensity ratio for change in α of 1, 2 or 3 degrees. The x-axis is the starting angle $α_0$. The intensity ratio was plotted as a value greater than unity.

We used this expression to calculate the relative change in intensity for changes in $\alpha$ of 1, 2 or 3 degrees (FIG. 2). If $\alpha_0$ is close to 0 or 90° the intensity ratio is strongly dependent on the polarizer angle $\alpha$. For example, a change in $\alpha$ from 45 to 46° changes the intensity ratio to 1.072, and a change of two degrees, 45 to 47°, results in a relative intensity change of 15%. Hence it appears that we must consider the sensitivity of the human eye to detecting relative intensities in adjacent images.

To answer the question of detectability of intensity differences we performed the following tests. We used a high concentration of rhodamine B (RhB) in ethanol to obtain a starting value near 45°. Next we inserted quartz plates in front of one side of the dual polarizer. The measured transmission of these plates were 93.4, 87.3, 81.8 and 76.1%, for one, two, three and four plates, respectively.

How many plates were needed to obtain a detectable intensity difference between the two sides of the dual polarizer? We were surprised that most of us could detect the presence of only one plate on either side of the dual polarizer. Everyone in the inventors' laboratory could recognize the presence of two plates, which provides an intensity difference of 1.14-fold or 14%. From these observations we judged that the average individual can detect an intensity ratio of 1.10, or a difference of 10%. This suggests that the polarizer angle can be adjusted to about 1.4 degrees in the worse case situation for $\alpha_0$ near 45°.

We repeated these tests using a hand lamp and a red filter transmitting above 590 nm, with no sample or reference solution. Once again we could recognize a difference due to just a single plate. For angles from 0 to 25°, or from 65 to 90°, it is probable that the accuracy of the polarizer angle can be greater than 1°. We did not perform such tests due to the limited resolution of our rotary stage. In summary, these results indicate that the accuracy in the polarizer angle should be 1° under most experimental conditions. This accuracy will be shown below to be adequate for typical sensing applications.

N-methyl-4-(pyrrolidinyl) styrylpyridinium iodide (MPSPI) was obtained from Molecular Probes, Eugene, Oreg., rhodamine B (RhB) was from Exciton, Inc., Dayton, Ohio, and 6-carboxy fluorescein (6-CF) was from Eastman Kodak, Rochester, N.Y. Intralipid (20%) was obtained from Kabi Vitrum, Inc., Clayton, N.C. and diluted 40-fold to 0.5%, in 50 mM tris buffer at the desired pH values.

Several excitation sources were used. We used a HeNe laser (543 nm) from Meles Griot, or a blue LED from Nichia Chemical Industries, Tokushima, Japan. When using an LED an excitation bandpass of 466±26 nm [26] was selected using a 510 nm short wavepass filter. We also used an electroluminescent device, which was obtained from Lumitek International, Inc., Ijamsville, Md. Its output was visually blue, with a maximum near 480 nm, and a half-width of 80 nm. Polarizing plastic films were from Rolyn Optics, Covina, Calif.

The fluorescence from RhB was observed through a 590 nm long pass glass filter, and 6-CF fluorescein was observed through a 540 nm wide band interference filter from Chroma Technology Corp.

Films of polyvinyl alcohol were prepared as described previously [27–28]. These films were physically stretched up to 6-fold to orient the MPSPI molecules and the film was then pressed against the side of the cuvette (FIG. 13). When using stretched films the stretching ratio ($R_S$) is defined as the axial ratio a/b of an ellipse which is formed when stretching an imaginary circle in the unoriented film [29]. The volume of the circle or ellipse is assumed to be conserved. Under these conditions $$R_S = N^{3/2} \quad (19)$$

where N is the physical fold of the stretch.

Stretched films provide an easily available reference fluorophore with a high polarization near unity. Such values can be obtained for fluorophores in stretched polymer films, which result in elongated fluorophores being aligned along the stretching axis [27]. In such systems the electronic transitions of the fluorophore are all aligned in one direction, or more precisely display a uniaxial orientation. The emission polarization from such samples are typically in the range of 0.6 to 0.8, and can approach 1.0. [28–29]. Stretched polymer films retain their orientation for extended periods of time, and thus can be practical for real-world applications.

Schematic diagrams of two possible geometries for visual polarization sensing are shown in FIG. 13. In the in-line geometry the light passes through the sample. In the front-face geometry the emission from the sample is viewed from the illuminated surface. In both cases the absorption of the stretched film is adjusted so that the exciting light is only partially absorbed, and adequate intensity remains to excite the sample. A filter is used to eliminate the excitation and to transmit the emission.

An important part of the visual polarization sensor is the dual polarizer (DP). This component consists of two adjacent sheet polarizers with the optical axis of one rotated 90° relative to the other polarizer (FIG. 13). If the sample is uniformly illuminated, the intensity transmitted by each half of the dual polarizer represents the parallel ($\|$) and perpendicular ($\perp$) components of the emission. This emission has two components, from the reference film and from the sample.

Visual detection of the degree of polarization may be accomplished by viewing the dual polarizer through an analyzer polarizer (P). This polarizer is rotated until the intensities are equal for both sides of the observation window. The total range of polarizer angles for the in-line geometry is 45°, as the emission ranges from 100% from the reference film to 100% from the sample. We found that it is easy to visually detect the position of equal intensities. As will be shown below, visual observation was found to provide 1° of accuracy in adjusting the analyzer polarizer.

The operating principle is the same whether the geometry is in-line or front face. However, the front-face geometry allows the use of an additional polarizer ($P_\perp$) after the stretched film but before the sample. This polarizer ($P_\perp$) can be used to selectively observe only the perpendicular component of the emission from the sample. As will be shown below, the use of $P_\perp$ increases the range of angles to 90°.

There are many advantages of polarization sensing with visual detection. One immediately obvious advantage is that a simple device may be used in practice of the invention. The only electronic component is the light source. Excitation could be accomplished with LEDs, laser diodes or electroluminescent devices, which may be powered using small batteries. Hence, such sensors will be extremely useful in emergency health care, doctor's offices and other medical applications. Additionally, the devices may be sufficiently inexpensive to allow their use in less critical situations such as bioprocessing and process control.

It should be noted that the visual polarization sensor relies on intensity ratios, and will thus be sensitive to any factor that alters the relative intensities of each polarized component. Hence the calibration curve will depend on the concentration and/or intensity of the sensing and reference fluorophores. If one fluorophore photobleaches at a rate different from the other fluorophore, then the calibration curve will change. However, visual polarization sensors may be used with large area/low intensity illumination, which should minimize photobleaching. Additionally, the inherent proximity focusing of the visual polarization sensor will avoid the intensity changes which occur with multiple optical components. Hence, a visual polarization sensor will provide stable readings for extended periods of time.

Polarization of an Oriented Film

Figure 3:
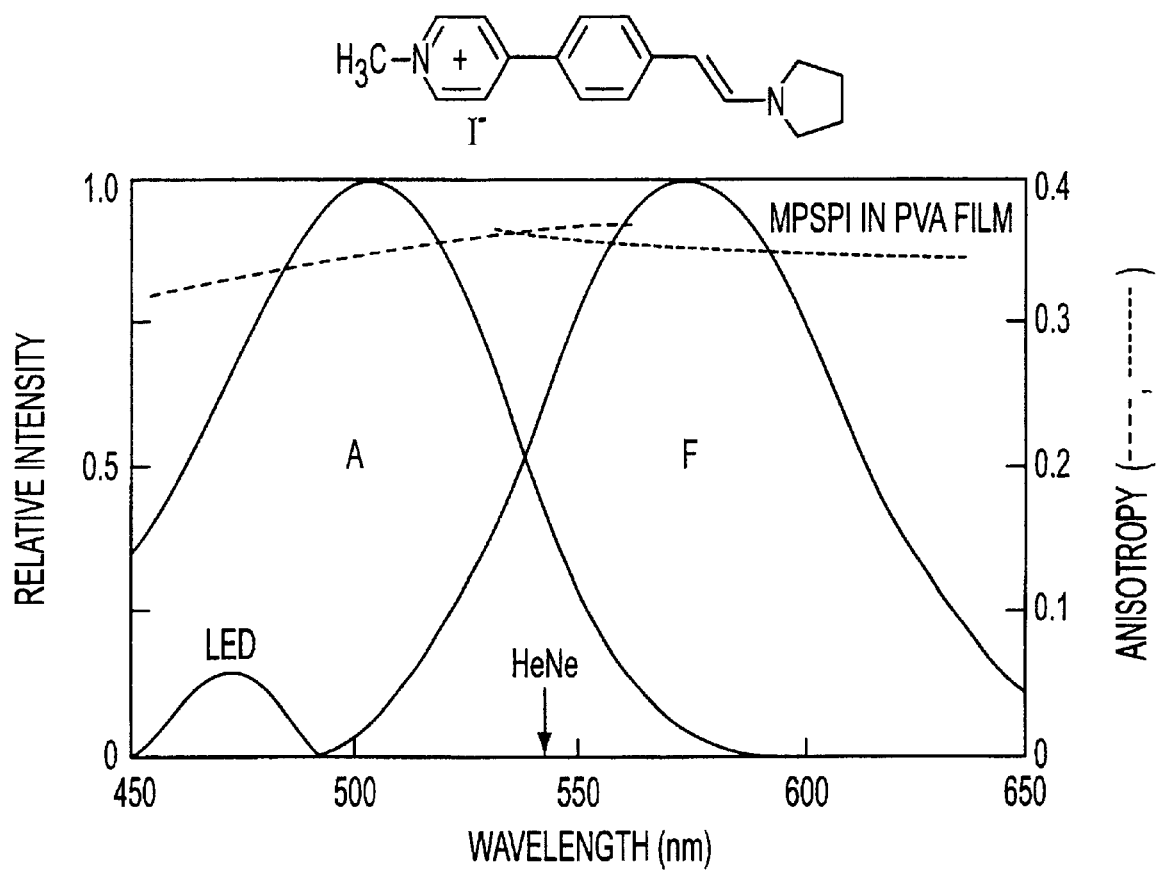
FIG. 3 shows the absorption and emission spectra of the reference fluorophore MPSPI in an unoriented polyvinyl alcohol film. Also shown are the excitation and emission anisotropy spectra in the PVA film. The excitation wavelengths available from the LED and HeNe laser are indicated on the x-axis.

Prior to showing examples of polarization sensing it is valuable to discuss the spectral properties of the reference film. We chose the dye MPSPI because of its favorable absorption and emission spectra and its large Stokes' shift (FIG. 3). MPSPI can be excited with either the 543 nm HeNe laser, or with the blue LED. Importantly, MPSPI displays a high fundamental anisotropy ($r_0$) across its absorption and emission spectra.

Figure 4:
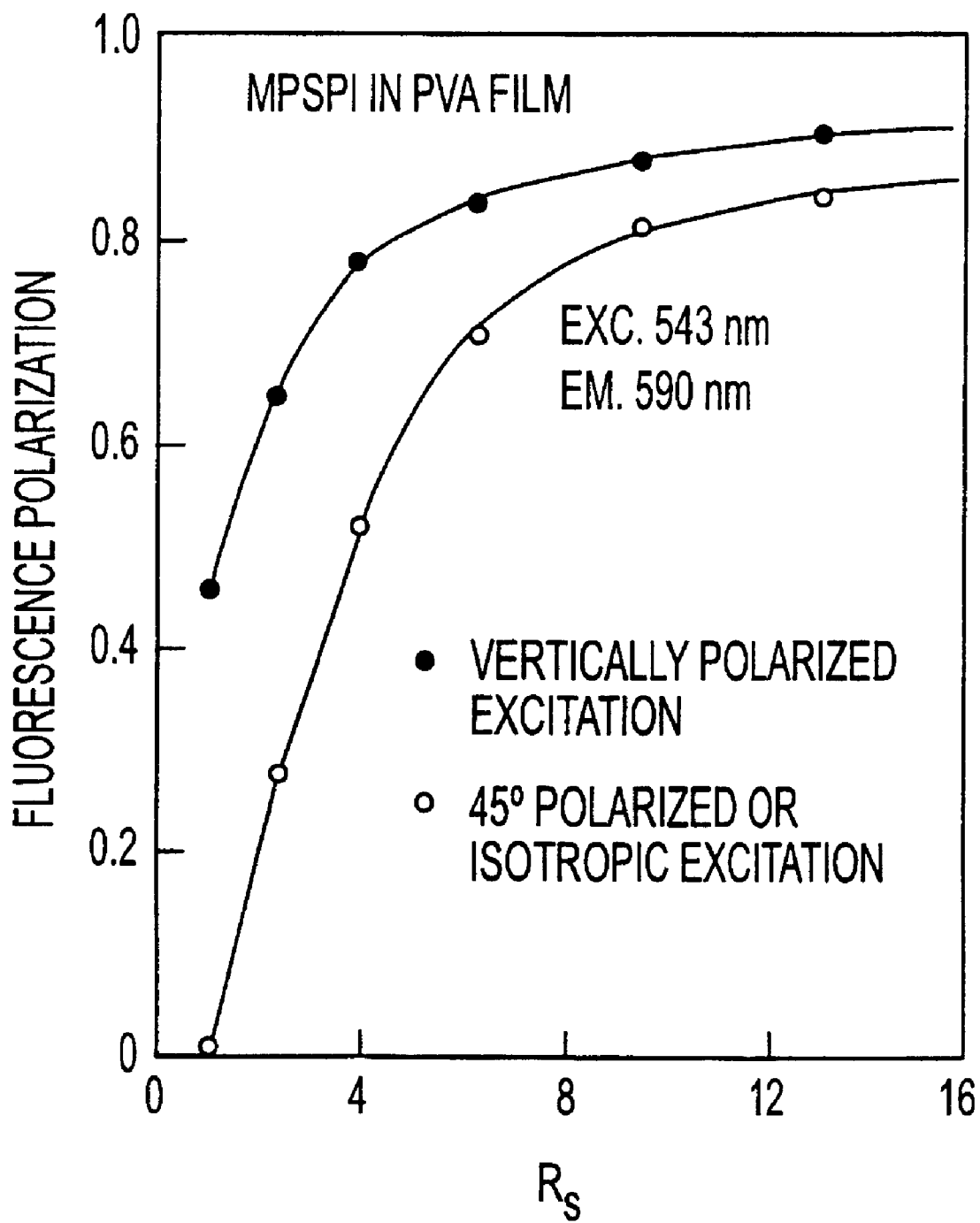
FIG. 4 shows the fluorescence polarization of MPSPI in the PVA film as a function of the stretching ratio. The stretching ratio $R_S$ is related to the actual physical fold of the stretch N by $R_S=N^{3/2}$ [29].

The elongated shape of MPSPI allows it to be strongly oriented in stretched PVA films. This is shown in FIG. 4 which shows the fluorescence polarization as a function of the stretching ratio. As the stretching ratio increases the polarization increases to over 0.8. It is valuable to notice that it is not necessary to use polarized excitation. The use of unpolarized excitation was mimicked by adjusting the excitation polarization at 45° from the vertical. Prior to stretching the polarization is near zero for unpolarized (45°) excitation. However, for the stretched samples this polarization increases to over 0.8. The increase in polarization occurs irrespective of whether the film is excited with vertically polarized or unpolarized light. Hence, polarized emission from the reference film can be obtained without an excitation polarizer.

The present invention will be further illustrated by means of the following non-limiting examples.

EXAMPLE 1

Polarization Sensing of RhB

Figure 5:
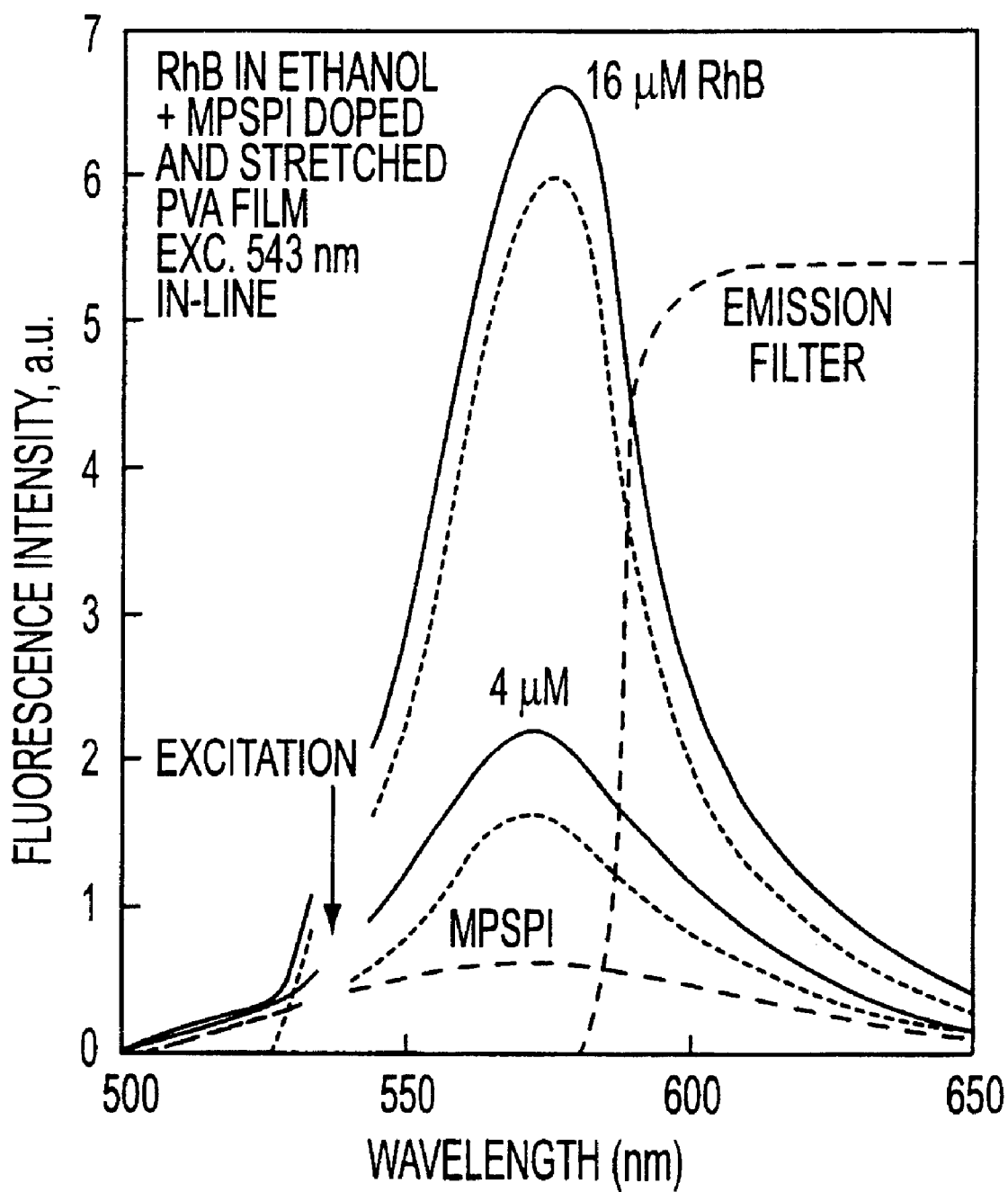
FIG. 5 shows the emission spectra of rhodamine B in ethanol with (-) and without ( . . . ) with the MPSPI reference. The dashed line (- - -) shows the emission spectrum of MPSPI alone. The additional dotted line shows the transmission profile of the emission filter.

To characterize the polarization sensor we examined solutions of rhodamine B (RhB) in ethanol at various RhB concentrations. Initially we use the in-line geometry (FIG. 13, top). Emission spectra are shown in FIG. 5 for excitation at 543 nm. RhB displays a narrow emission with an emission maximum near 575 nm. The emission maximum of the MPSPI reference is at a similar wavelength, but the emission spectra of MPSPI is somewhat broader than RhB. As the RhB concentration increases, its emission becomes dominant over that of the MPSPI reference. For the polarization measurements the combined emission of MPSPI and RhB was observed using a filter which transmits above 580 nm.

Figure 6:
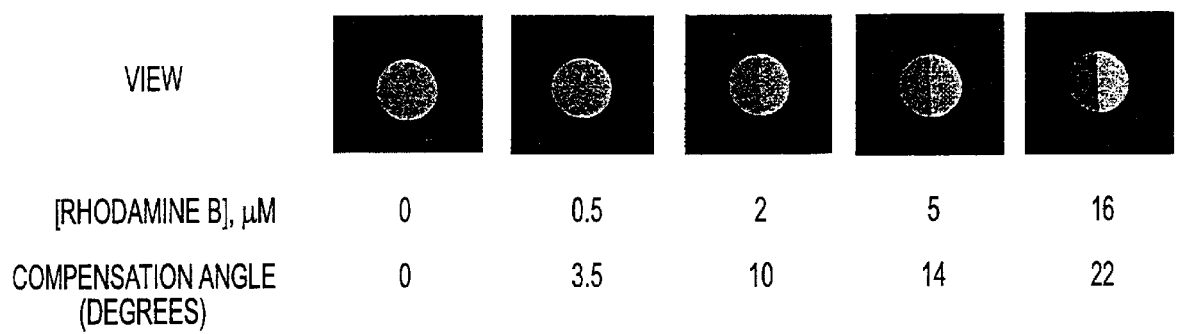
FIG. 6 shows the emitted light observed through the analyzer polarizer (P) for different concentrations of rhodamine B using the MPSPI reference and the in-line geometry. The position of the analyzer polarizer is at $\alpha_0$ near 75° for all images. The listed values are the compensation angles ($\Delta\alpha$) needed to equalize the intensities.

FIG. 6 shows the visual images seen through the analyzer polarizer for increasing concentrations of RhB. The polarization angle was initially adjusted to yield equal intensities in the absence of RhB. Since the reference film is highly polarized the initial value $\alpha_0$ is near 75°. All images were recorded with the analyzer polarizer in this same position. As the RhB concentration increases, the intensities through each side of the dual polarizer become unequal. The direction of the intensity changes can be understood by noting that the right side contains the horizontal polarizer and the emission from RhB is unpolarized. Addition of RhB results in an increased relative intensity on the right side, where the dual polarizer and the analyzer polarizer are in the horizontal position. The intensity increase is weaker on the left side where the polarizers (DP and analyzer) are nearly crossed.

Figure 7:
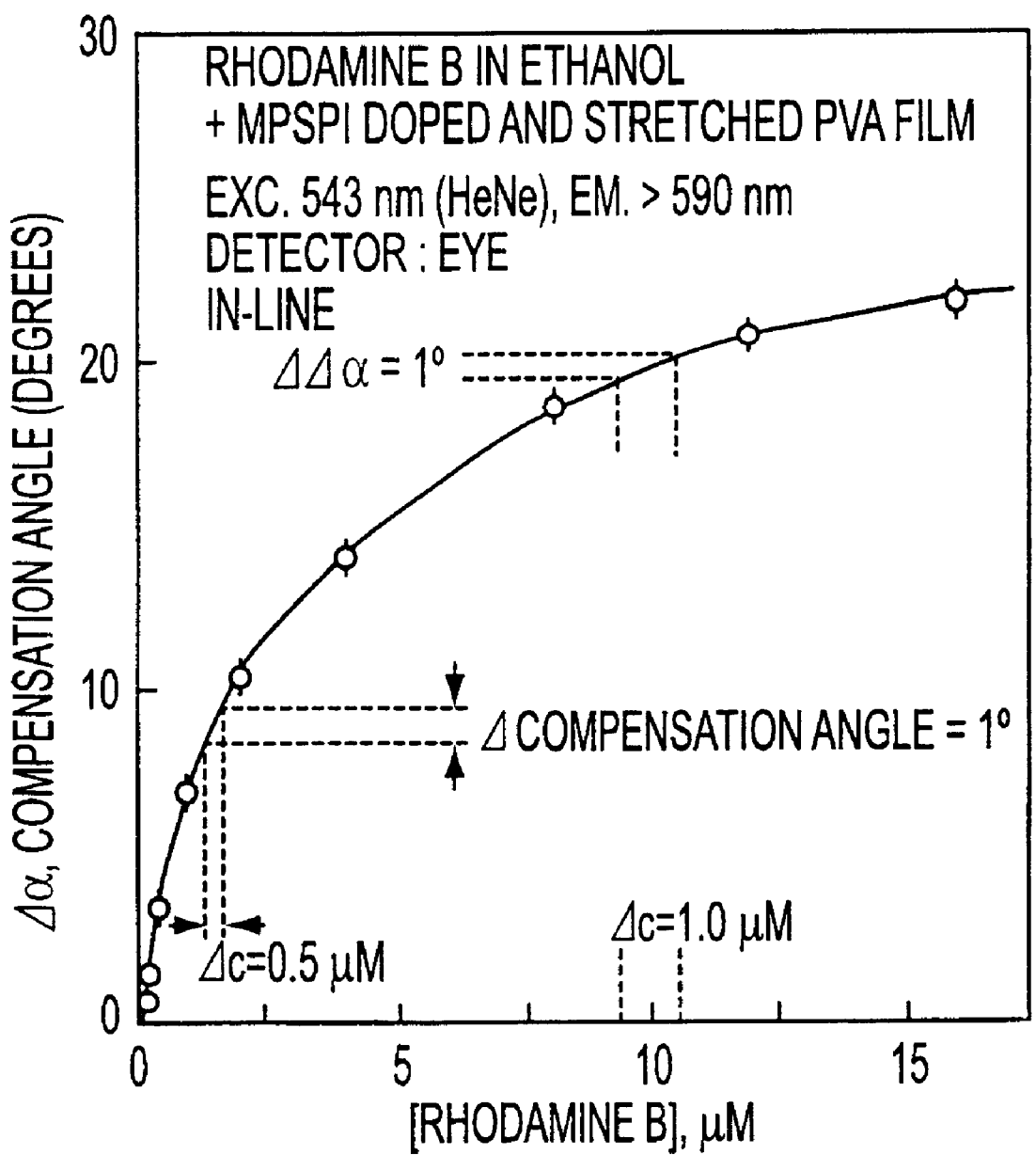
FIG. 7 shows the dependence of the compensation angle ($\Delta\alpha$) on the concentration of rhodamine B using the in-line geometry. The uncertainty in the compensation angle is shown as $\Delta\Delta\alpha$.

Next we examined the changes in the polarizer angle, the compensation angle, needed to equalize the intensities seen from each half of the dual polarizer (FIG. 7). To determine the compensation angle we measured the difference between the analyzer angles needed to equalize the intensities in the absence and presence of the RhB sample. As the RhB concentration increased to 15 $\mu$M, the compensation angle increased by over 20° degrees. During these measurements we asked several members of this laboratory to adjust the polarizer and measure the difference angle $\Delta\alpha$. Most individuals measured the same value of $\Delta\alpha$ to within 1 degree. It is interesting to consider the uncertainty in the RhB concentration resulting from the 1° uncertainty in the compensation angle. At low RhB concentrations the uncertainty in 0.5 $\mu$M, or about one part in four. At higher RhB concentrations the uncertainty is about 1 $\mu$M, or one part in ten. While this accuracy is somewhat poor, it is probably adequate for some clinical determinations, particularly those which report a yes/no answer rather than a specific value. We note that the range of concentrations is determined by the brightness of the reference film. Lower fluorophore concentrations could be measured if the reference film is less fluorescent.

EXAMPLE 2

Fluorophores in Scattering Media

In many situations it is desirable to measure the fluorescence from tissues, which can be due to intrinsic tissue fluorescence or due to extrinsic probes. Such measurements are becoming more important with the development of red or near infra-red (NIR) probes [30–32] and with the use of these probes for trans-dermal measurements [33–34]. Hence we decided to test the visual polarization sensor to measure the concentration of RhB in 0.5% intralipid. Such solutions are highly scattering, and mimic the scattering properties of skin.

Figure 8:
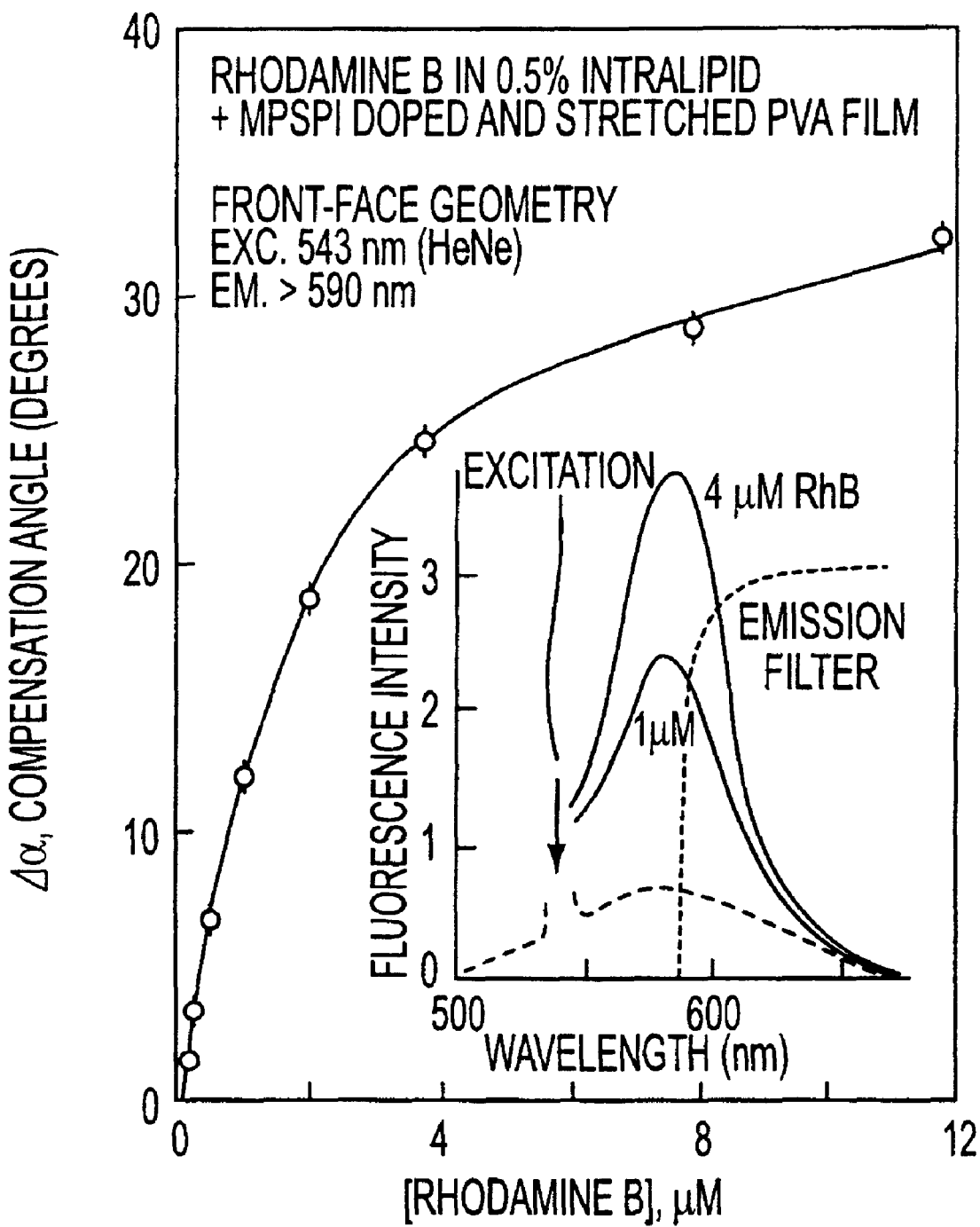
FIG. 8 shows the dependence of the compensation angle on the rhodamine B concentration in 0.5% intralipid. These data were obtained using the front-face geometry. The insert shows the emission spectra observed for the rhodamine B-MPSPI sample. The dashed line emission spectrum is of the MPSPI reference alone.

As for the previous case, RhB and MPSPI were excited at 543 nm using a HeNe laser. In this case we used the front face geometry, as shown in FIG. 13 (lower panel), including the polarizer ($P_\perp$) in front of the sample. The compensation angles are shown in FIG. 8. Compared to the previous data for the in-line geometry (FIG. 7), the front face geometry results in a wider range of compensation angles, up to 30° or larger. This wider range is due to the additional polarizer ($P_\perp$) which selected only the horizontal component of the RhB emission. We did not notice any decrease in resolution due to the intralipid.

We note that it is not obvious that one can use polarization measurements to measure fluorophore concentrations in scattering media. It is well known that light scattering results in depolarization of the emission from fluorophores within the scattering media. In the present situation this effect is not important because the polarization is imposed on the emission after it exits the scattering media.

EXAMPLE 3
Polarization Sensing of pH

As a practical illustration of polarization sensing we used 6-carboxy fluorescein (6-CF) as a pH-sensitive fluorophore. Fluorescein has been widely used as a pH-sensitive probe [35–37]. The pH-dependent fluorescence intensity is due to the carboxy group. Fluorescein is highly fluorescent at higher pH values where this group is ionized, and more weakly fluorescent at low pH. The intensity of fluorescein and its carboxy derivatives increases dramatically over the pH range from 5 to 8.

Figure 9:
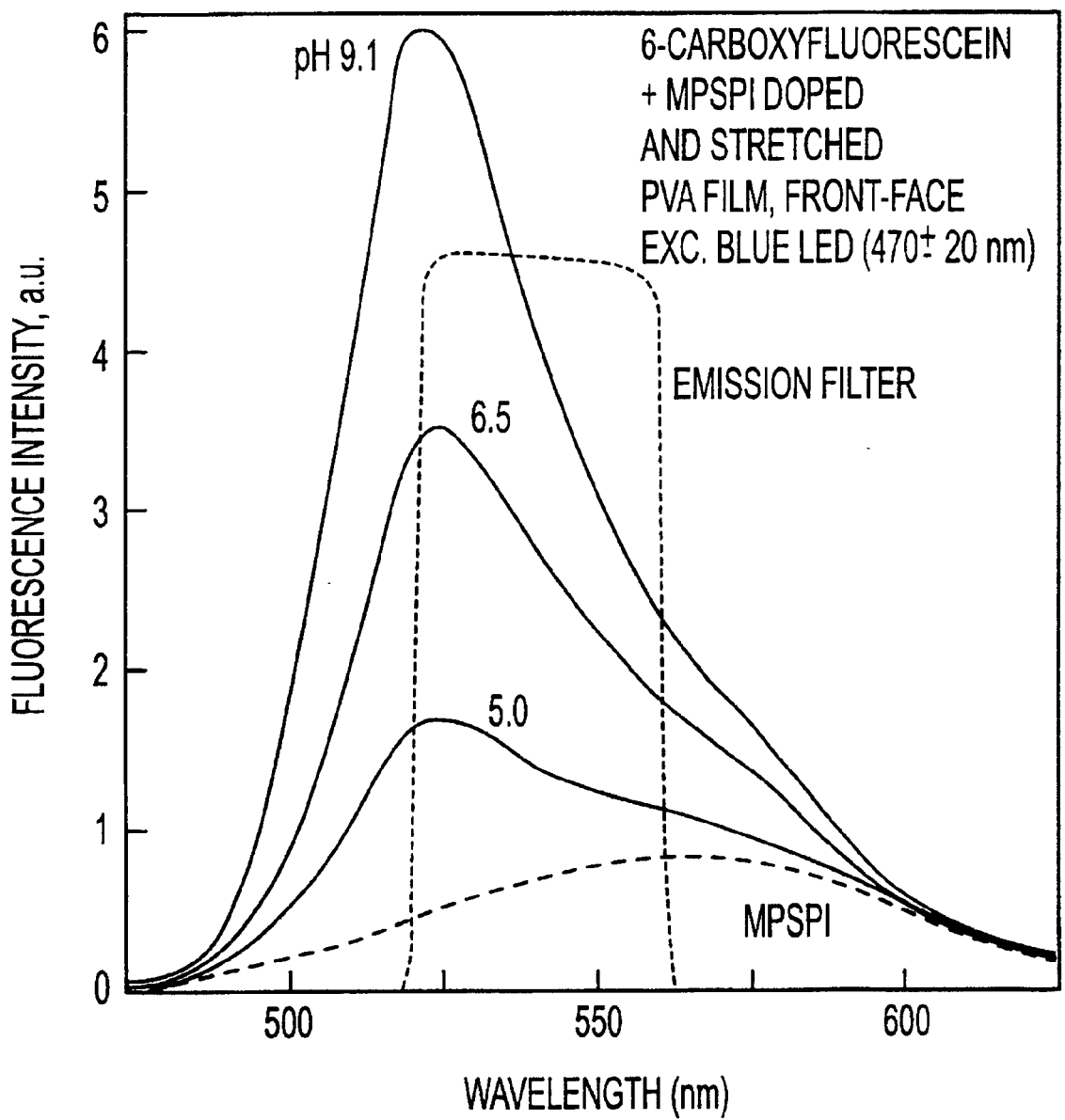
FIG. 9 shows the emission spectra of a front-face anisotropy pH sensor based on 6-carboxyfluorescein. The dashed line shows the transmission profile of the emission filter used for the visual measurements.

FIG. 9 shows the emission spectrum of fluorescein in the front-face geometry, including the reference MPSPI film. In this case excitation was accomplished with the 470 nm output of a blue light emitting diode (LED). This solid state light source can be powered by a 9 volt battery. The fluorescein emission at 525 nm increases about 5-fold from pH 5 to 9. The emission of the MPSPI reference is at somewhat longer wavelengths. This illustrates one minor technical challenge in the design of a visual polarization sensor, the colors on each side of the dual polarizer can be slightly different due to the different relative intensities of the fluorophore and the reference. In the present case we minimized these visual differences by selecting a relatively narrow range of wavelengths for visual observation, from 540 to 560 nm. In practice it should not be difficult to obtain similar visual colors for this sample and reference emission. A wide variety of fluorescent sensors are available [8], and a large number of fluorophores can be oriented in stretched films [27].

Figure 10:
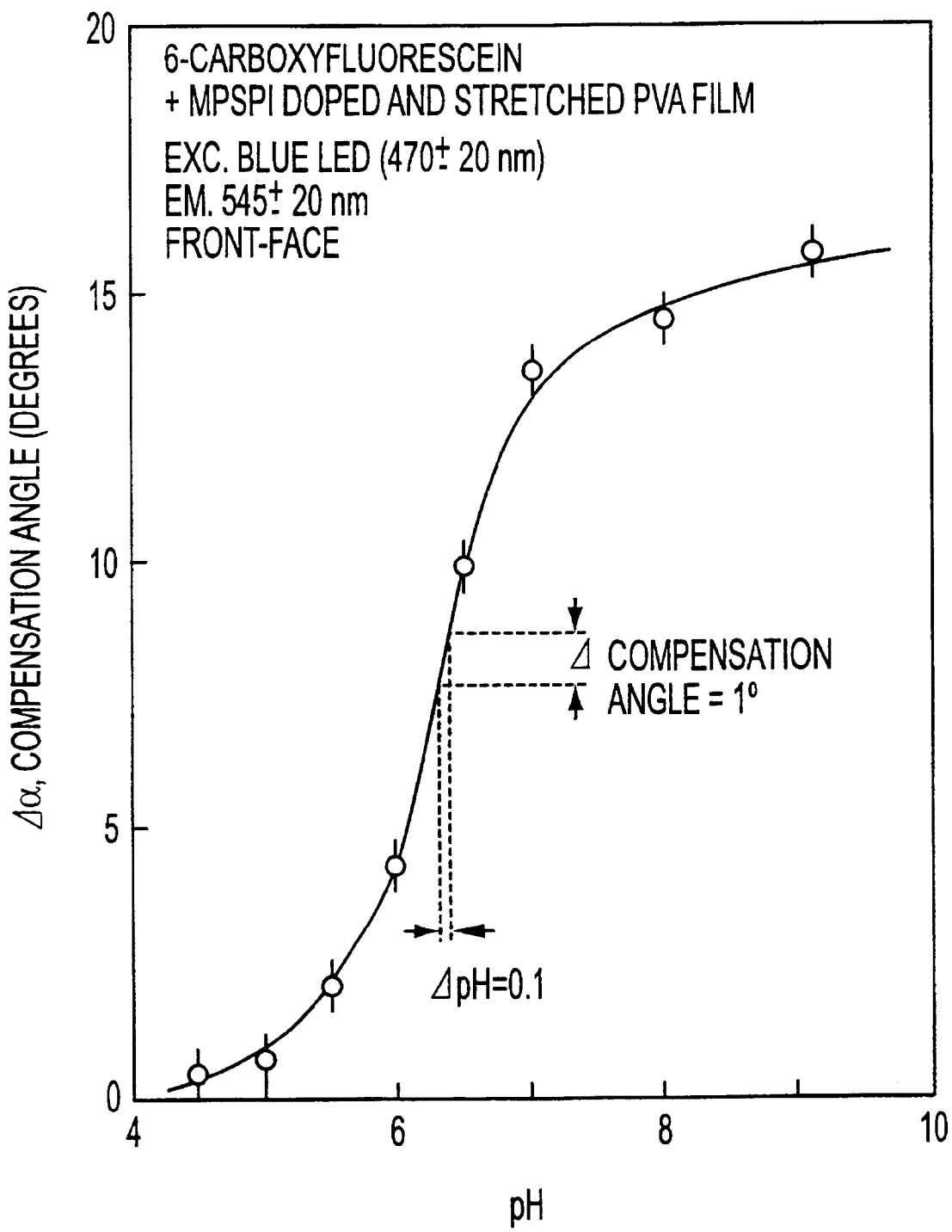
FIG. 10 shows the compensation angles for the front-face polarization pH sensor.

Compensation angles for the polarization pH sensor are shown in FIG. 10. These angles display the usual sigmoidal behavior for a pH sensor. For this initial visual pH sensor the one degree accuracy of the compensation angle results in a pH accuracy to ±0.1 pH unit at the center of the titration curve. For clinical pH measurements the required accuracy is ±0.02 [38–40]. Hence, the present sensor is not adequate for use in blood gas measurements. However, an accuracy of ±0.1 pH unit is adequate in a wide range of less critical applications. We note that the pH accuracy is less than ±0.1 pH unit at pH values away from the central pH value near 6.5. This is a characteristic of any optical indicator which is based on a single dissociation constant.

It should be noted that the approach used for the fluorescein-polarization sensor can be applied to a wide variety of analytes. The only requirement is a fluorophore which changes intensity in response to the analyte. Such fluorescent probes are known for a wide variety of species, including sodium, potassium, calcium, magnesium, zinc, chloride, phosphate and oxygen [41–50]. Hence, visual sensors can be anticipated for a wide range of analytes.

Figure 11:
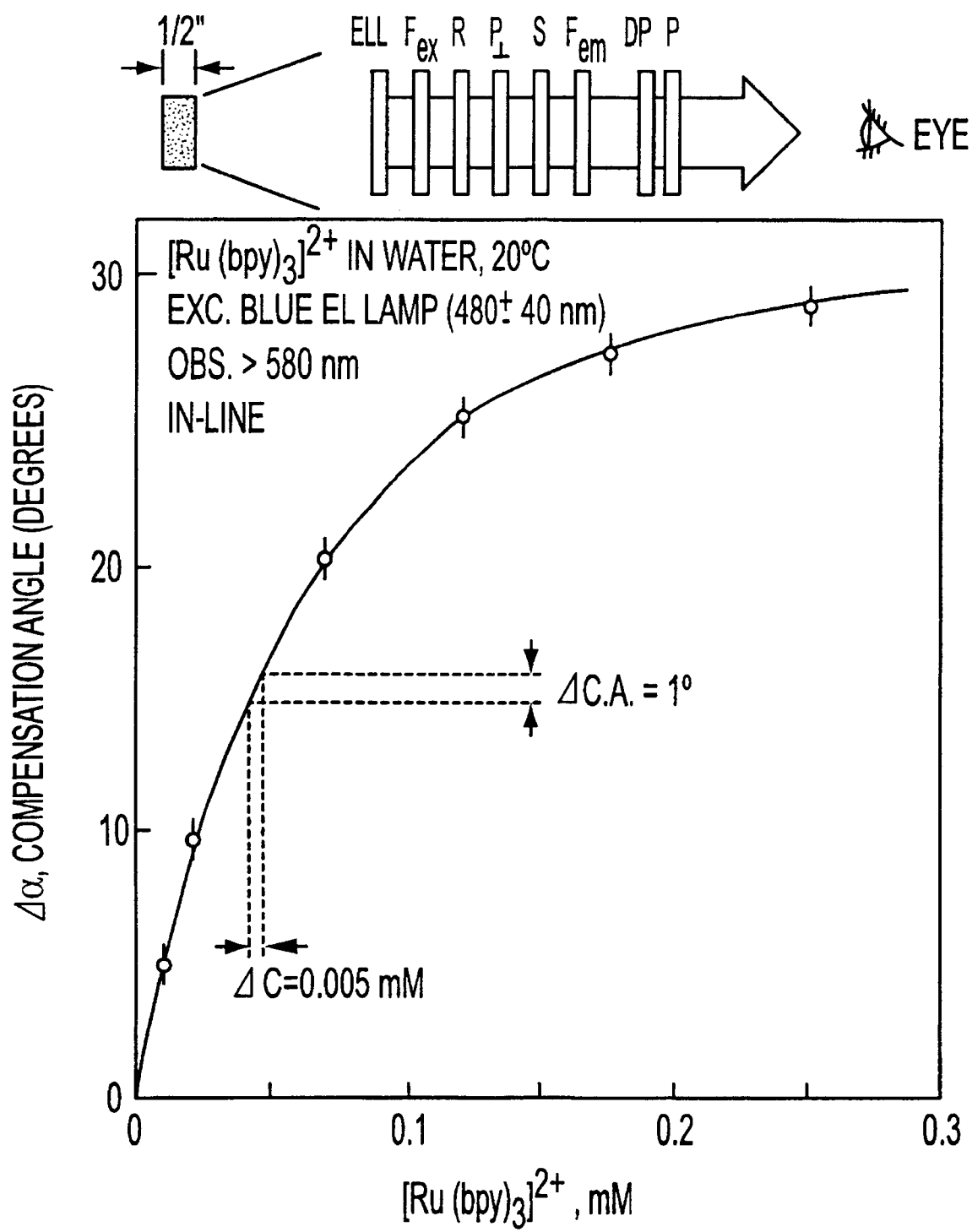
FIG. 11 shows the visual detection of the concentration of $[Ru(bpy)_3]^{2+}$ measured using the same compound $[Ru(bpy)_3]^{2+}$ as the reference. ELL, electroluminescent light source; $F_{ex}$, excitation filter; R, reference solution with a constant concentration of $[Ru(bpy)_3]^{2+}$, $P_\perp$, polarizer; S, sample with varying concentrations of $[Ru(bpy)_3]^{2+}$, $F_{em}$, emission filter; DP, dual polarizer; P, analyzer polarizer.
Figure 12A:
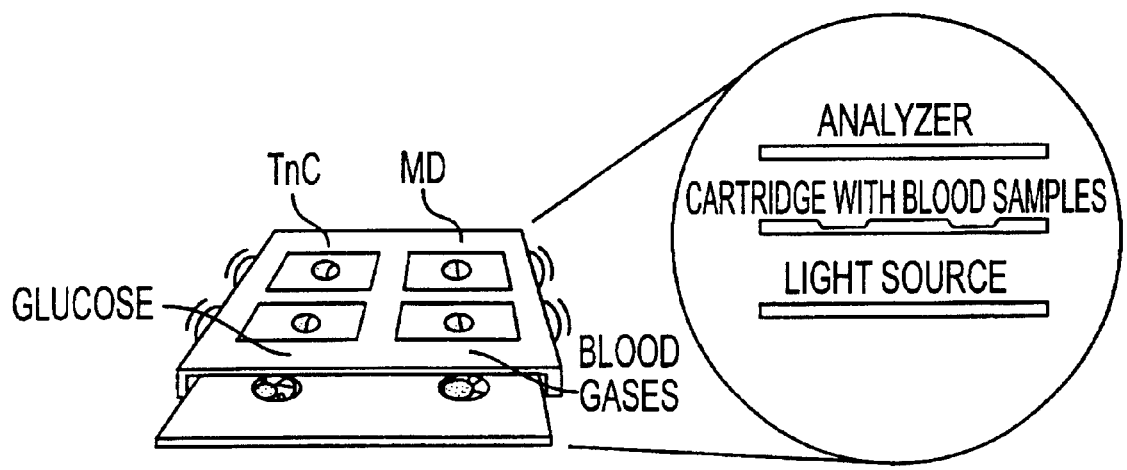
FIG. 12A depicts one embodiment of a blood chemistry device according to the present invention. The excitation source, sample and detector are in an in-line geometry.
Figure 12B:
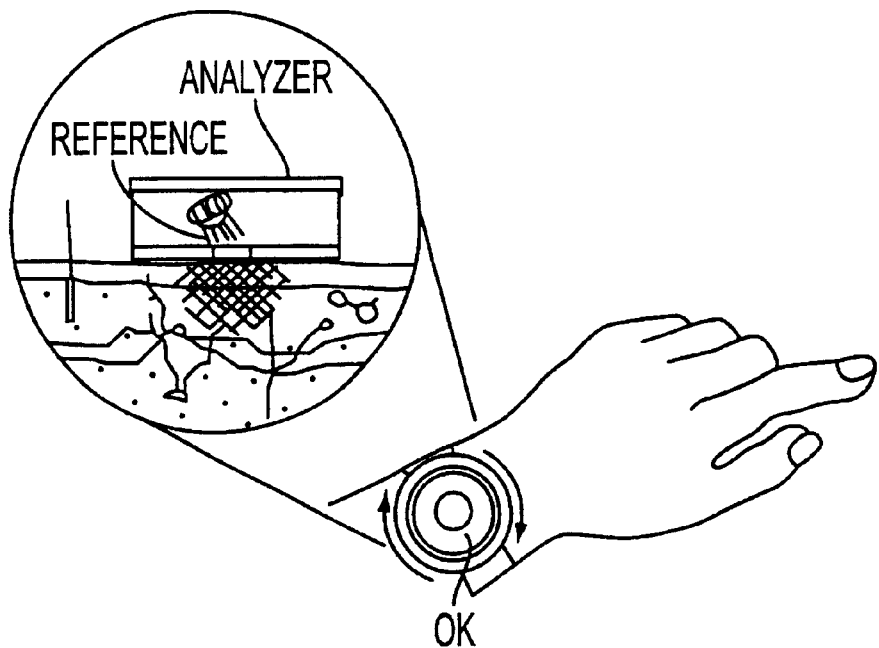
FIG. 12B depicts another device which analyses data from an implantable patch. The fluorescence from the implanted patch and/or tissue is observed using front-face geometry.

EXAMPLE 4
Visual Polarization Sensing Using the Same Substance as the Reference In this example, we show how the measurement can be accomplished using the same fluorophore as the sample and as the reference. This possibility was discussed above (FIG. 13 and FIG. 1) where we described the use of an additional polarizer in front of the sample to select the perpendicular component of the sample emission. The optical arrangement is shown in FIG. 11 (top). In this case the light source was an electroluminescent device which was powered by a 9 volt battery. The output from the ELL was blue and centered near 480 nm.

To illustrate this method of visual sensing we used a sample which contained varying concentrations of $[Ru(bpy)_3]^{2+}$. Such metal ligand complexes are now being widely used as luminescent probes when covalently attached to macromolecules [51–55] and as chemical sensors [56–61]. As the reference we used the same fluorophore $[Ru(bpy)_3]^{2+}$ at a constant concentration. The emission from this reference sample was viewed through a polarizer ($P_\perp$) to select just the perpendicular component at its emission. The combined emission from the sample and reference was then viewed through the dual-polarizer analyzer-polarizer combination. The optical arrangement is shown on the top of FIG. 11.

The compensation angles for various concentrations of $[Ru(bpy)_3]^{2+}$ are shown in FIG. 11. These angles are the differences between the polarizer angles needed to equalize up the intensities in the absence and presence of the indicated $[Ru(bpy)_3]^{2+}$ concentration. These results demonstrated that visual polarization sensing is possible using the same fluorophore as the reference. This approach has the advantages of automatically providing the same visual wavelengths for the sample and reference, and thereby avoiding any difference in color on each side of the dual polarizer.

It should be noted that these results suggest the use of visual polarization sensing in a number of common applications. Luminescent metal ligand complexes have been used in immunoassays [53–54], so that one can anticipate visual immunoassays based on intensity changes of metal-ligand complexes. Visual immunoassays may also be possible with the usual fluorophores with nanosecond decay times. Changes in the luminescence intensity can be caused by energy transfer or a variety of other mechanisms [62–63]. Another possible application is for industrial or household determination of oxygen, pH or salt concentrations. Metal-ligand probes are known which are sensitive to oxygen [56–57] or pH [60], and probes are known which are quenched by chloride [48–49]. Hence, one could develop visual sensors for these common analytes.

EXAMPLE 5

Figure 16:
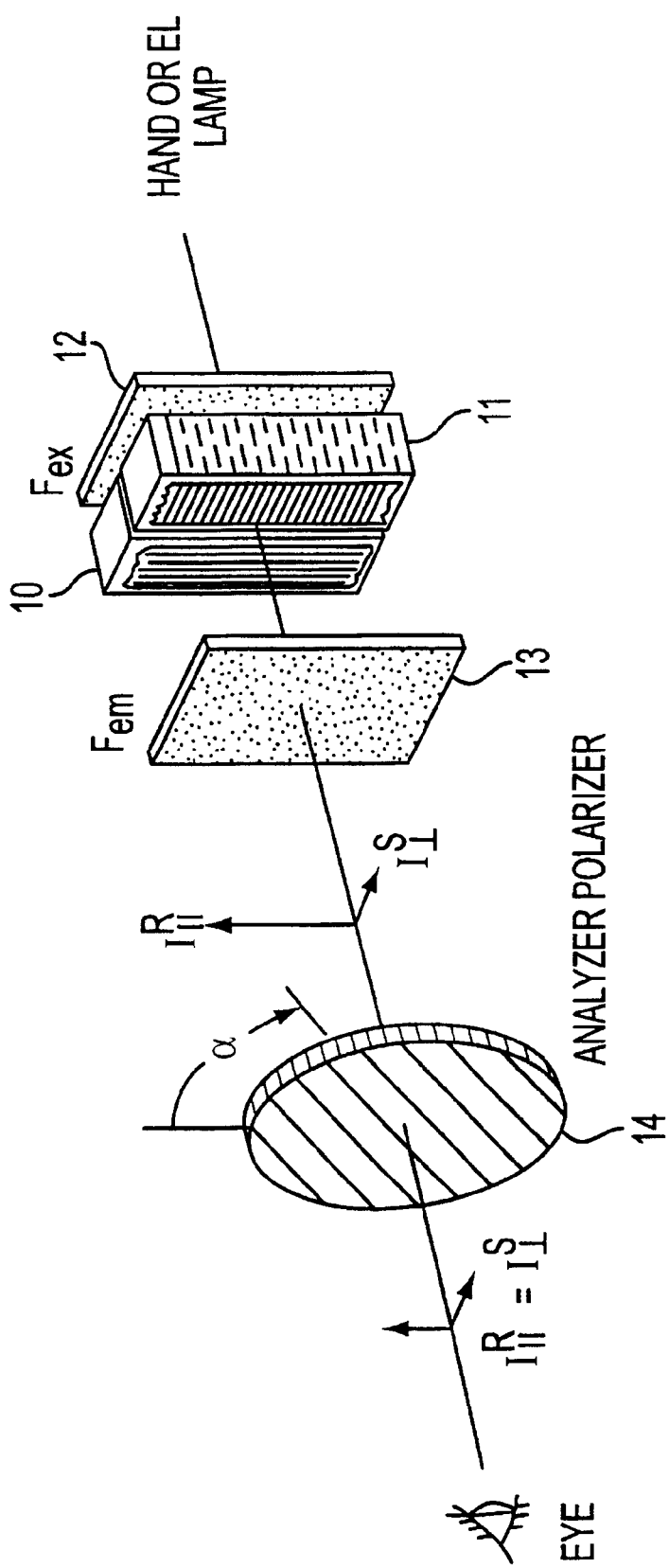
FIG. 16 schematically depicts an apparatus for polarization sensing with visual detection according to the present invention. The value of $\alpha$ is 0° when the analyzer polarizer is oriented vertically.

In this example, the sensing of glucose and calcium using the FIG. 16 apparatus is described. In FIG. 16, the reference and sensing molecules are housed in containers 10 and 11, respectively. Containers 10 and 11 have associated therewith a vertical and horizontal polarizer film, respectively. The excitation light travels from the source (not shown) through filter 12, then through containers 10 and 11, then through filter 13, then finally through analyzer polarizer 14. The analyzer polarizer 14 may be rotated until the adjacent intensities from the vertically and horizontally polarized emission are equalized. The angle of the analyzer polarizer is used to determine the analyte concentration.

The glucose assay was accomplished using the glucose/galactose binding protein from *E. Coli* (GGBP). We used a mutant which contained a single cysteine residue at position 26 (Q26C GGBP) [19]. This protein was labeled with (4'iodoacetamidoanilino)-naphthalene-6-sulfonic acid (I-ANS) from Molecular Probes, Inc. A solution containing 2.5 mg/ml Q26C GGBP in 20 mM phosphate, 1 mM tris-(2-carboxyethyl)phosphine (TCEP), pH 7.0 was reacted with 50 μL of a 20 mM solution of I-ANS in tetrahydrofuran (purchased from Molecular Probes, Inc.). The resulting labeled protein was separated from the free dye by passing the solution through a Sephadex G-25 column. The protein-ANS conjugate was purified further on Sephadex G-100 and dissolved in 20 mM phosphate, pH 7.0. The labeled protein was used as both the reference and the sensing molecule.

The calcium assay was performed using Fluo-3 was obtained from Molecular Probes, Inc. as both the reference and the sensing molecule. The calcium concentration was controlled using the calcium buffer kits, C-3009, also from Molecular Probes, Inc.

Figure 17A:
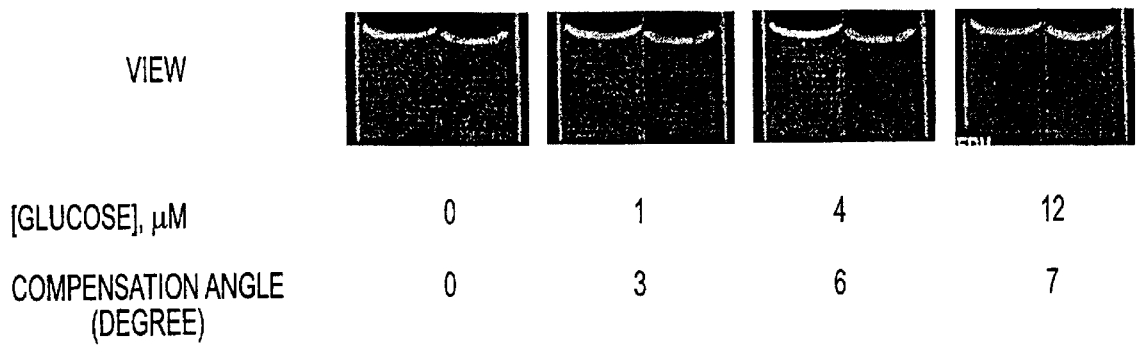
FIGS. 17A and B are images seen through the analyzer for different concentrations of glucose (FIG. 17A) and calcium (FIG. 17B). In each case the initial angle of the analyzer was adjusted to yield equal intensities in the absence of glucose on calcium. The images were then recorded at the same analyzer angle. The values under the images are the analyzer angles needed to equalize the intensities, not the angle needed to equalize the intensities.
Figure 17B:
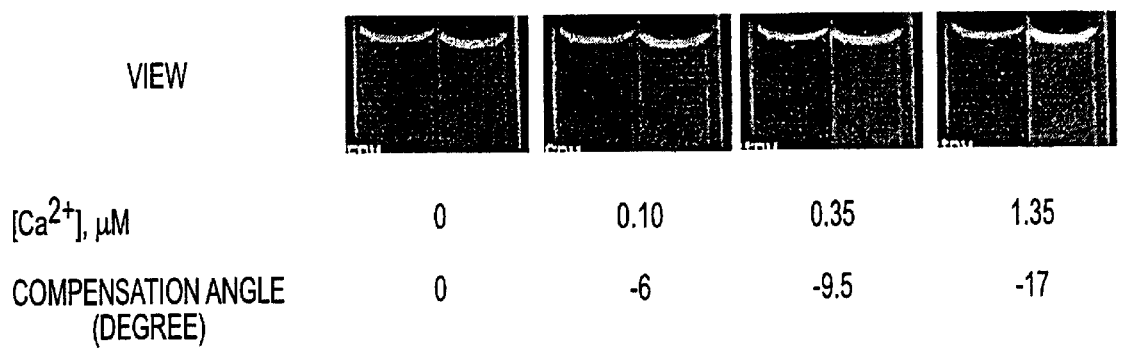

The images seen through the analyzer polarizer are shown in FIG. 17. For these images the initial angular rotation of the analyzer ($\alpha_0$) was adjusted to match the intensities seen from both sides of the sensor. The images were then recorded for various analyze concentrations, with the analyzer left in the same angular position ($\alpha_0$). As the glucose concentration increases the intensity from the horizontal (right) side of the sensor decreases, as can be seen in the top panel of FIG. 17. As the calcium concentration increases the intensity in the horizontal (right) side of the sensor decreases, as can be seen in the lower panel.

The angular position of the analyzer can be adjusted to yield visually equivalent intensities. These angles are shown under the images in FIG. 17. For glucose the angles of the analyzer must be increased to equalize the intensities. This effect is due to the decreased horizontal intensity, and the need to increase the horizontal intensity to visually match both sides of the sensor. For increasing concentrations of calcium the angle of the analyzer must be decreased to equalize the intensities. This direction of change is needed because the increased intensity from the horizontal component must be attenuated to yield visually equivalent intensities.

Figure 18:
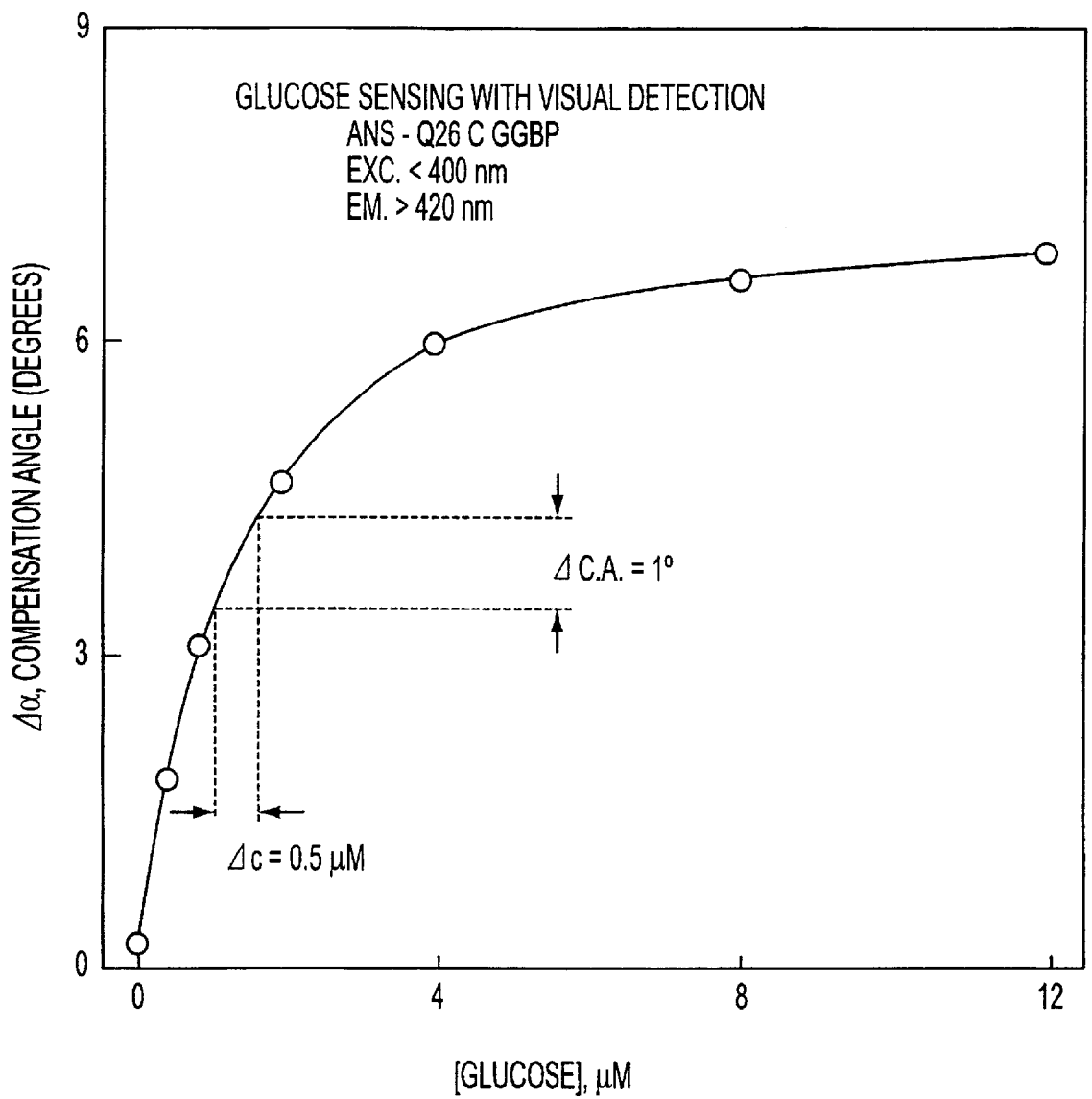
FIG. 18 depicts the calibration curve for glucose sensing with visual detection.
Figure 19A:
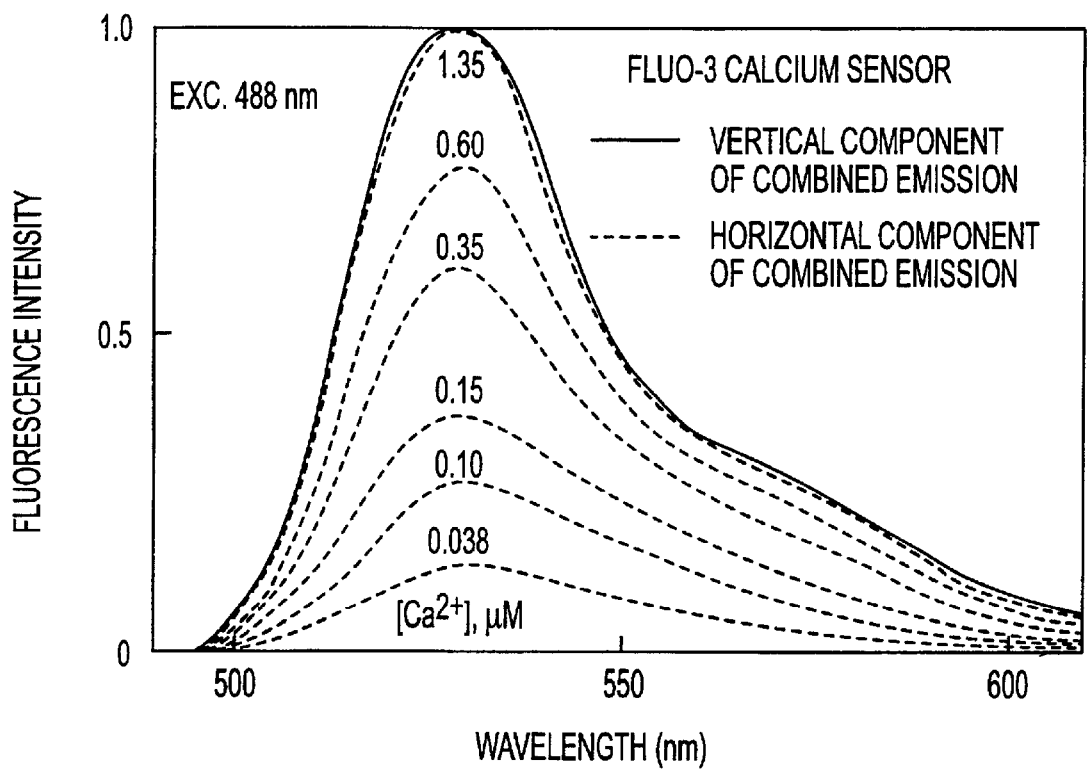
FIGS. 19A and B depict the polarization sensing of calcium using Fluo-3.
Figure 19B:
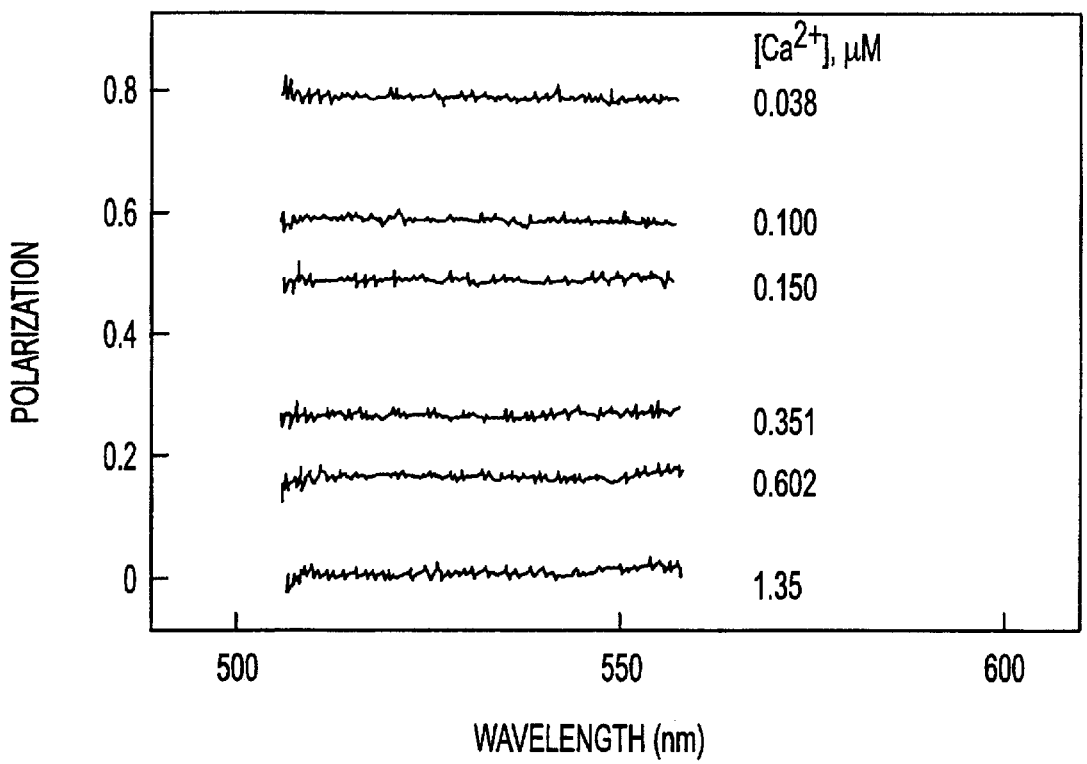
FIG. 19B shows the polarization across the emission spectra.
Figure 20:
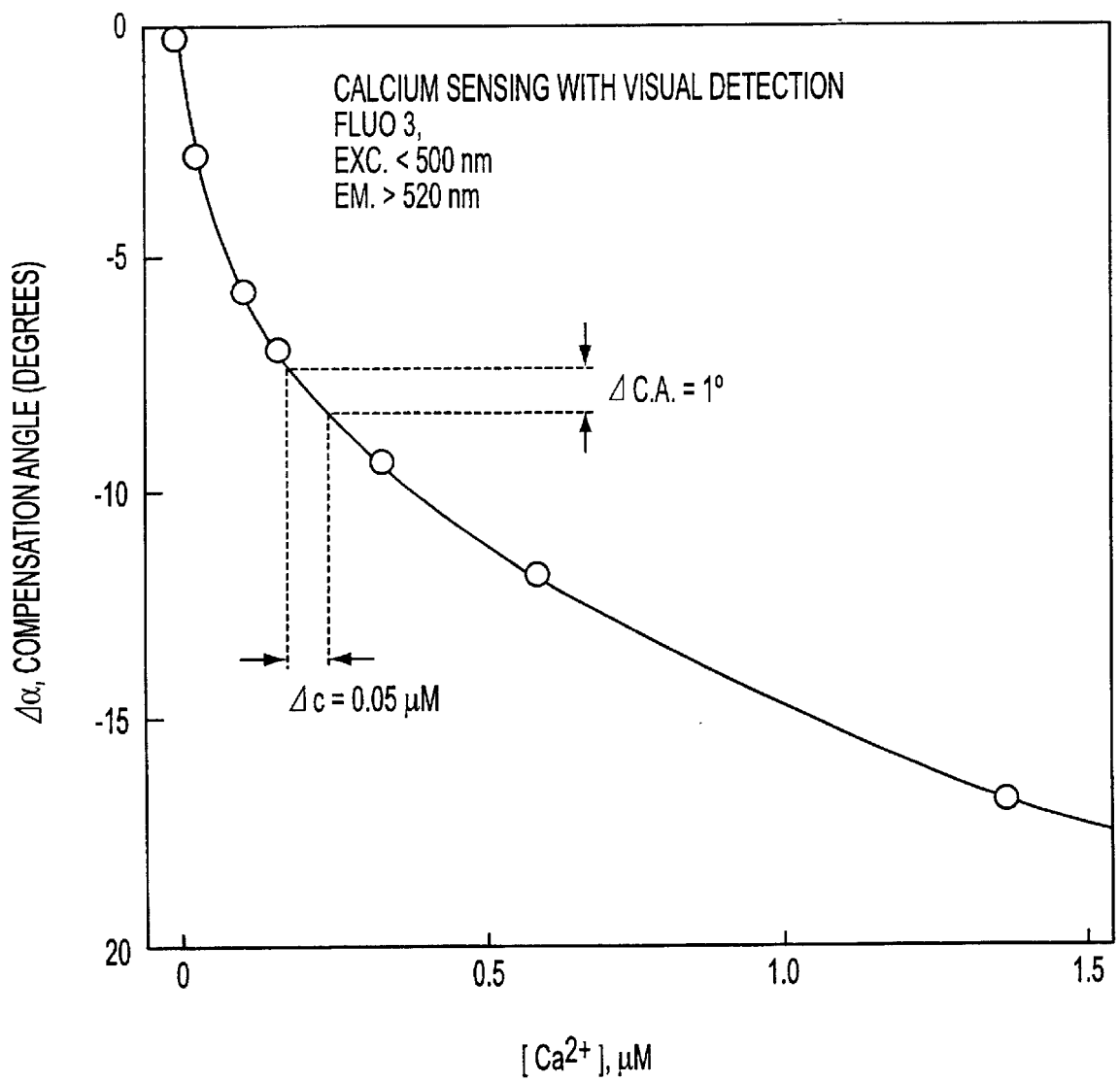
FIG. 20 depicts the calibration curve for calcium sensing with visual detection.

FIGS. 18 and 20 show the calibration curves for the compensation angles for glucose and calcium, respectively. We have found that the compensation angles are typically accurate to 1 or 2 degrees [64]. An accuracy of 1 degree in the compensation angle results in an accuracy of $\pm 0.5 \mu M$ in glucose and $\pm 0.05 \mu M$ in calcium, as found for the most sensitive part of the curve. While the accuracy is somewhat less than available with electronic detection, the accuracy may be adequate for some clinical or analytical applications, particularly where a yes/no answer is adequate.

REFERENCES

1. Spichiger-Keller, U. E. (1998). *Chemical Sensors and Biosensors for Medical and Biological Applications*, Wiley-VCH, New York, pp. 413.
2. Kunz, R. E., Ed. (1997). Proc. of 3rd European Conference on Optical Chemical Sensors and Biosensors, Europt(R)odeIII. *Sensors and Actuators B*, Elsevier Publishers, New York, B38, pp. 1–188, and B39, pp. 1–468.
3. Thompson, R. B. (Ed.) (1997). *Advances in Fluorescence Sensing Technology III, SPIE Proc.*, Volume 2980, pp. 582.
4. Lakowicz, J. R., Ed. (1994). Topics. in *Fluorescence Spectroscopy, Volume 4: Probe Design and Chemical Sensing*, Plenum Press, New York, pp. 501.
5. Schulman, S. G., Ed. (1993). *Molecular Luminescence Spectroscopy, Methods and Applications: Part 3*, John Wiley & Sons, Inc., New York, pp. 467.
6. Wolfbeis, O. S., Ed. (1991). *Fiber Optic Chemical Sensors and Biosensors, Volume I*, CRC Press, Boca Raton, pp. 413.
7. Wolfbeis, O. S., Ed. (1991). *Fiber Optic Chemical Sensors and Biosensors, Volume II*, CRC Press, Boca Raton, pp. 358.
8. Haugland, R. P. (1996). *Handbook of Fluorescent Probes and Research Chemicals*, Molecular Probes, Inc., Eugene, Oreg. (T. Z. Spence, Ed.), pp. 679.
9. Slavik, J. (Ed.) (1998). *Fluorescence Microscopy and Fluorescent Probes, Vol. 2*, Plenum Press, New York, pp. 272.
10. Czarnik, A. W. (Ed.) (1993). *Fluorescent Chemosensors for Ion and Molecule Recognition*, ACS Symposium Series, American Chemical Society, pp. 235.
11. Lippitsch, M. E., Draxler, S., and Kieslinger, D. (1997). Luminescence lifetime-based sensing: new materials, new devices, *Sensors and Actuators* B 38–39:96–102.
12. Lippitsch, M. E., Pusterhofer, J., Leiner, M. J. P., and Wolfbeis, O. S. (1988). Fibre-optic oxygen sensor with the fluorescence decay time as the information carrier, *Anal. Chim. Acta* 205:1–6.
13. Szmacinski, H., and Lakowicz, J. R. (1994). "Lifetime-based sensing," in *Topics in Fluorescence Spectroscopy: Vol. 4: Probe Design and Chemical Sensing* (J. R. Lakowicz, Ed.), Plenum Press, New York, pp. 295–334.
14. Terpetschnig, E., Szmacinski, H., and Lakowicz, J. R. (1997). Long-lifetime metal-ligand complexes as probes in biophysics and clinical chemistry, *Methods in Enzymology*, Academic Press, pp. 295–321.
15. Szmacinski, H., Castellano, F. N., Terpetschnig, E., Dattelbaum, J. D., Lakowicz, J. R., and Meyer, G. J. (1997). Long-lifetime Ru(II) complexes for the measurement of high molecular weight protein hydrodynamics, *Biochim. et. Biophys. Acta* 1383:151–159.
16. Klimant, I., and Wolfbeis, O. S. (1998). Dual luminophore referenced optodes: A convenient way to convert the fluorescence intensity into a phase shift or time dependent parameter, *Europt(r)ode IV*, German Chemical Society, pp. 125–126.
17. Neurauter, G., Klimant, I., Liebsch, G., Kosch, U., and Wolfbeis, O. S. (1998). A comparative study on different types of intensity independent optical $pCO_2$ sensors, *Europt(r)ode IV*, German Chemical Society, pp. 231–232.
18. Lakowicz, J. R., Castellano, F. N., Dattelbaum, J. D., Tolosa, L., Rao, G., and Gryczynski, I. (1998). Low frequency modulation sensors using nanosecond fluorophores, *Anal. Chem.*, 70:5115–5121.
19. Tolosa, L., Gryczynski, I., Eichhorn, L., Dattelbaum, J. D., Castellano, F. N., Rao, G., and Lakowicz, J. R. (1999). Glucose sensor for low cost lifetime-based sensing using a genetically engineered protein, *Anal. Biochem.*, 267(1):114–20.
20. Lakowicz, J. R., Dattelbaum, J. D., and Gryczynski, I. (1998). Quantitative intensity measurements in scattering media, *Sensors and Actuators*, submitted.
21. Abugo, O., Gryczynski, Z., and Lakowicz, J. R. (1998). Modulation sensing of fluorophores in tissue—A new approach to drug compliance monitoring, *J. Biomedical Optics*, submitted.
22. Lakowicz, J. R., Gryczynski, I., Gryczynski, Z., and Dattelbaum, J. D. (1999). Anisotropy based sensing with reference fluorophores, *Anal. Biochem.*, 267:397–405.
23. Jabloński, A. (1960). On the notion of emission anisotropy, *Bull. Acad. Pol. Sci.* 8:259–264.
24. Weber, G. (1952). Polarization of the fluorescence of macromolecules. I. Theory and experimental method, *Biochemical Journal* 51:145–155.

25. Lakowicz, J. R. (1999). *Principles of Fluorescence Spectroscopy*, 2nd Edition, Chapter 10, Plenum Publishes, Inc., New York, in press.
26. Sipior, J., Carter, G. M., Lakowicz, J. R., and Rao, G. (1996). Single quantum well light emitting diodes demonstrating as excitation sources for nanosecond phase-modulation fluorescence lifetime measurements, *Rev. Sci. Instrum.* 67(11):3795–3798.
27. Michl, J., and Thulstrup, E. W. (1986). *Spectroscopy With Polarized Light*, VCH Publishers, New York, pp. 573.
28. Kawski, A., and Gryczynski, Z. (1987). On the determination of transition-moment directions from absorption anisotropy measurements, *Z. Naturforsch.* 42a: 617–621.
29. Kawski, A., Gryczynski, Z., Gryczynski, I., Lakowicz, J. R., and Piszczek, G. (1996).
Photoselection of luminescent molecules in anisotropic media in the case of two-photon excitation. Part II. Experimental studies of Hoechst 33342 in stretched poly(vinyl alcohol) films, *Z. Naturforsch.* 51a:1037–1041.
30. Daehne, S., Resch-Genger, U., and Wolfbeis, O. S., Eds. (1998). *Near-Infrared Dyes for High Technology Applications, Proc. of the NATO Advanced Research Workshop on Syntheses*, Czech Republic, pp. 468.
31. Thompson, R. B. (1994). Red and near-infrared fluorometry, in *Topics in Fluorescence Spectroscopy, Vol. 4: Probe Design and Chemical Sensing*, (J. R. Lakowicz, Ed.), Plenum Press, New York, pp. 151–181.
32. Casay, G. A., Shealy, D. B., and Patonay, G. (1994). Near-infrared fluorescence probes, in *Topics in Fluorescence Spectroscopy, Vol. 4: Probe Design and Chemical Sensing*, (J. R. Lakowicz, Ed.), Plenum Press, New York, pp. 183–222.
33. Bambot, S. B., Rao, G., Romauld, M., Carter, G. M., Sipior, J., Terpetschnig, E., and Lakowicz, J. R. (1995). Sensing oxygen through skin using a red diode laser and fluorescence lifetimes, *Biosensors & Bioelectronics*, 10(6/7):643–652.
34. Szmacinski, H., and Lakowicz, J. R. (1996).
Frequency-domain lifetime measurements and sensing in highly scattering media, *Sensors and Actuators B*, 30:207–215.
35. Babcock, D. F. (1983). Examination of the intracellular ionic environment and of ionophore action by null point measurements employing the fluorescein chromophore, *J. Biol. Chem.* 258:6380–6389.
36. Klonis, N., Clayton, A. H. A., Voss, E. W., and Sawyer, W. H. (1998). Spectral properties of fluorescein in solvent-water mixtures: Applications as a probe of hydrogen bonding environments in biological systems, *Photochem. Photobiol.* 67:500–510.
37. Molecular Probes Catalogue (1996). Sixth Edition, Richard P. Haugland, Ed., pp. 551–561.
38. Mahutte, C. K., Holody, M., Maxwell, T. P., Chen, P. A., and Sasse, S. A. (1994). Development of a patient-dedicated, on-demand, blood gas monitor, *Am. J. Respir. Crit. Care Med.* 149:852–859.
39. Mahutte, C. K., Sasse, S. A., Chen, P. A., and Holody, M. (1994). Performance of a patient-dedicated, on-demand blood gas monitor in medical ICU patients, *Am. J. Respir. Crit. Care Med.* 150:865–869.
40. Mahutte, C. K. (1994). Continuous intra-arterial blood gas monitoring, *Intensive Care Med.* 20:85–86.
41. Tsien, R. Y. (1989). Fluorescent indicators of ion concentrations in *Methods in Cell Biology*, Academic Press, New York, pp. 127–156.
42. Kao, J. P. Y. (1994). Practical aspects of measuring $[Ca^{2+}]$ with fluorescent indicators in *Methods in Cell Biology*, Academic Press, New York, 40:155–181.
43. Lakowicz, J. R., Szmacinski, H., and Johnson, M. L. (1992). Calcium concentration imaging using fluorescence lifetime and long-wavelength probes, *J. Fluoresc.* 2(1):47–62.
44. Lakowicz, J. R., and Szmacinski, H. (1992). Fluorescence lifetime-based sensing of pH, $Ca^{2+}$, $K^+$ and glucose, *Sensors and Actuators B* 11:133–143.
45. Kao, J. P. Y., Harootunian, A. T., and Tsien, R. Y. (1989). Photochemically generated cytosolic calcium pulses and their detection by Fluo-3, *J. Biol. Chem.* 264:8179–8184.
46. Valeur, B. (1994). "Principles of fluorescent probe design for ion recognition," in *Topics in Fluorescence Spectroscopy, Vol. 4: Probe Design and Chemical Sensing* (J. R. Lakowicz, Ed.), Plenum Press, New York, pp. 21–48.
47. Czarnik, A. W. (1994). "Fluorescent chemosensors for cations, anions, and neutral analytes," in *Topics in Fluorescence Spectroscopy, Vol. 4: Probe Design and Chemical Sensing* (J. R. Lakowicz, Ed.), Plenum Press, New York, pp. 49–70.
48. Verkman, A. S., Sellers, M. C., Chao, A. C. Leung, T., and Ketcham, R. (1989). Synthesis and characterization of improved chloride-sensitive fluorescent indicators for biological applications, *Anal. Biochem.* 178:355–361.
49. Biwersi, J., Tulk, B., and Verkman, A. S. (1994). Long-wavelength chloride-sensitive fluorescent indicators, *Anal. Biochem.* 219:139–143.
50. Bacon, J. R., and Demas, J. N. (1987). Determination of oxygen concentrations by luminescence quenching of a polymer immobilized transition metal complex, *Anal. Chem.* 59:2780–2785.
51. Terpetschnig, E., Szmacinski, H., and Lakowicz, J. R. (1997). Long-lifetime metal-ligand complexes as probes in biophysics and clinical chemistry, in *Methods and Enzymology*, Academic Press, New York, 278:294–321.
52. Szmacinski, H., Terpetschnig, E., and Lakowicz, J. R. (1996). Synthesis and evaluation of Ru-complexes as anisotropy probes for protein hydrodynamics and immunoassays of high-molecular weight antigens, *Biophys. Chem.* 62:109–120.
53. Youn, H. J., Terpetschnig, E., Szmacinski, H., and Lakowicz, J. R. (1995). Fluorescence energy transfer immunoassay based on a long-lifetime luminescent metal-ligand complex, *Anal. Biochem.* 232:24–30.
54. Terpetschnig, E., Szmacinski, H., and Lakowicz, J. R. (1995). Fluorescence polarization immunoassay of a high-molecular weight antigen based on a long-lifetime Ru-ligand complex, *Anal. Biochem.* 227:140–147.
55. Guo, X-Q., Castellano, F. N., Li, L., Szmacinski, H., Lakowicz, J. R., and Sipior, J. (1997). A long-lived, highly luminescent Re(I) metal-ligand complex as a biomolecular probe, *Anal. Biochem.* 254:179–186.
56. Carraway, E. R., Demas, J. N., and DeGraff, B. A. (1991). Luminescence quenching mechanism for microheterogeneous systems, *Anal. Chem.* 63:332–336.

57. Demas, J. N., and DeGraff, B. A. (1991). Design and applications of highly luminescent transition metal complexes, *Anal. Chem.* 63:829A-837A.

58. Weidner, S., and Pikramenou, Z. (1998). Photoactive ruthenium(II) cylodextrins responsive to guest binding, *Chem. Commun.* pp. 1473–1474.

59. Chang, Q., Lakowicz, J. R., and Rao, G. (1997). Fluorescence lifetime-based sensing of methanol, *Analyst.* 122:173–177.

60. Murtaza, Z., Chang, Q., Rao, G., Lin, H., and Lakowicz, J. R. (1997). Long-lifetime metal-ligand pH probe, *Anal. Biochem.* 247:216–222.

61. Demas, J. N., and DeGraff, B. A. (1994). Design and applications of highly luminescent transition metal complexes, in *Topics in Fluorescence Spectroscopy, Vol. 4: Probe Design and Chemical Sensing*, (J. R. Lakowicz, Ed.), Plenum Press, New York, pp. 71–107.

62. Ozinskas, A. J., Malak, H., Joshi, J., Szmacinski, H., Britz, J., Thompson, R. B., Koen, P. A., and Lakowicz, J. R. (1992). Homogeneous model immunoassay of thyroxine by phase-modulation fluorescence spectroscopy, *Anal. Biochem.* 213:264–270.

63. Hemmila, I. A. (1992). *Applications of Fluorescence in Immunoassays*, John Wiley & Sons, New York, pp. 343.

64. Gryczynski, I., Gryczynski, Z., and Lakowicz, J. R., *Anal. Chem.*, in press (1999).

We claim:

1. A method for determining the presence or concentration of an analyte in a sample, comprising the steps of:
   a) providing a fluorescent reference molecule and a fluorescent sensing molecule;
   b) exposing said sensing molecule to a medium containing an analyte to form a mixture, wherein said analyte is capable of changing the intensity of the fluorescence emitted by the sensing molecule in a concentration-dependent manner;
   c) exposing said reference molecule and said mixture to a radiation source which causes said reference and sensing molecules to emit fluorescence;
   d) polarizing said emitted fluorescence along two different polarization axes which are substantially perpendicular to each other;
   e) attenuating the emission from one of the polarization axes, if necessary, such that the intensities of the emissions through both axes are substantially equal; and
   f) correlating the degree of attenuation with the presence or concentration of said analyte in said sample.

2. The method of claim 1, wherein the determination of emission intensity in step e) is performed visually.

3. The method of claim 1, wherein the determination of emission intensity in step e) is performed electronically.

4. The method of claim 3, wherein the electronic determination of emission intensity is performed by independently measuring the two intensities.

5. The method of claim 3, wherein the electronic determination of emission intensity includes measurement in a balancing circuit.

6. The method of claim 3, wherein the electronic determination of emission intensity includes measurement of the ratio of the two intensities.

7. The method of claim 1, wherein step d) is performed by allowing the emitted fluorescence to pass through a dual polarizer.

8. The method of claim 1, wherein the polarized emission is passed through a rotatable polarizer; wherein the attenuation is performed by rotating said polarizer; and wherein said correlation includes determining the amount of rotation of said polarizer.

9. The method of claim 1, wherein the fluorescent reference molecule is attached to a film.

10. The method of claim 9, wherein the film is a stretched polymeric film.

11. The method of claim 1, which further comprises filtering said emitted fluorescence to substantially eliminate scattered excitation.

12. The method of claim 1, wherein the reference molecule and the sensing molecule are distinct entities having the same structure, and the reference molecule is isolated from the analyte.

13. The method of claim 1, wherein the analyte is selected from the group consisting of oxygen, glucose, blood gases, proteins and ions.

14. A sensor for determining the presence or concentration of an analyte in a sample, which comprises:
   a) means for maintaining a fluorescent reference molecule;
   b) means for maintaining a fluorescent sensing molecule, wherein said analyte is capable of changing the intensity of the fluorescence emitted by the sensing molecule in a concentration-dependent manner;
   c) optionally a radiation source which is capable of causing said reference and sensing molecules to emit fluorescence;
   d) means for polarizing said emitted fluorescence along two different polarization axes which are substantially perpendicular to each other; and
   e) means for attenuating the emission from one of the polarization axes, such that the intensities of the emissions through both axes are substantially equal.

15. The sensor of claim 14, which further comprises electronic means for the determination of the intensity of said emitted fluorescence.

16. The sensor of claim 14, wherein component d) comprises a dual polarizer.

17. The sensor of claim 14, wherein component e) comprises a rotatable polarizer.

18. The sensor of claim 14, wherein the fluorescent reference molecule is attached to a film.

19. The sensor of claim 18, wherein the film is a stretched polymeric film.

20. The sensor of claim 14, which further comprises means for filtering said emitted fluorescence to substantially eliminate scattered excitation.

21. The sensor of claim 14, wherein the radiation source is external to the sensor.

22. The sensor of claim 21, wherein the light source is selected from the group consisting of sunlight and room light.

* * * * *